United States Patent

Pedersen et al.

[11] Patent Number: 5,886,104
[45] Date of Patent: Mar. 23, 1999

[54] GRAFTED CROSS-LINKED POLYOLEFIN SUBSTRATES FOR PEPTIDE SYNTHESIS AND ASSAYS

[75] Inventors: Walther Batsberg Pedersen, Rosenhavestraede; Kristoffer Almdal, Nyvel; Lars Winther, Ved Ungdomsboligerne; Rolf Henrik Berg, Strandvaenget, all of Denmark

[73] Assignee: Forskniingscenter Riso, Roskilde, Denmark

[21] Appl. No.: 569,255

[22] PCT Filed: Jun. 20, 1994

[86] PCT No.: PCT/DK94/00245

§ 371 Date: Dec. 18, 1995

§ 102(e) Date: Dec. 18, 1995

[87] PCT Pub. No.: WO95/00533

PCT Pub. Date: Jan. 5, 1995

[30] Foreign Application Priority Data

Jun. 18, 1993 [DK] Denmark .................................. 0724/93

[51] Int. Cl.⁶ ........................... C08F 255/02; C12Q 1/00; G01N 33/545
[52] U.S. Cl. ....................... 525/242; 525/333.3; 525/374; 436/518; 436/531; 436/532; 436/535
[58] Field of Search .................................. 525/242, 333.3, 525/374; 436/518, 531, 532, 535

[56] References Cited

U.S. PATENT DOCUMENTS 3,795,664  3/1974  Tregear et al. .
4,234,663  11/1980 Catte et al. .............................. 428/517
4,908,405  3/1990  Bayer et al. ............................. 525/330
5,133,878  7/1992  Gsell et al. ............................. 210/767
5,258,454  11/1993 Berg et al. ............................ 525/54.11

FOREIGN PATENT DOCUMENTS 0 480 643 A2  4/1992  European Pat. Off. .
1 234 982     6/1971  United Kingdom .
WO 90/02749   3/1990  WIPO .
WO 91/13098   9/1991  WIPO .

*Primary Examiner*—Jeffrey Mullis
*Attorney, Agent, or Firm*—Foley, Hoag & Eliot LLP; Anita Varma; Beth Arnold

[57] ABSTRACT

A solid support for the solid-phase synthesis of peptides or proteins in high yield and in high purity, suited both to the synthesis of a single peptide or protein and to the parallel and substantially simultaneous synthesis of a plurality thereof, is based on a cross-linked polyolefin, especially polyethylene, substrate, the cross-linking having been obtained by irradiation with high energy electrons or γ radiation or treatment with organic peroxide such as benzoyl peroxide, to which substrate are grafted polymer chains such as polystyrene chains which are functionalized with a chemical functionality facilitating the formation of an anchoring linkage between the polymer moiety and another chemical species. The solid support is also suited for use in solid-phase biosystems, notably bioassays, such as immunoassays, DNA hybridization assays or PCR amplification. The grafted chains may bear substituents which are such that the polymer-grafted cross-linked polyolefin substrate is swellable by water or aqueous media, in other words, hydrophilic, which makes the solid support particularly well suited for assays of the ELISA type.

22 Claims, 5 Drawing Sheets

GRAFTED CROSS-LINKED POLYOLEFIN SUBSTRATES FOR PEPTIDE SYNTHESIS AND ASSAYS

FIELD OF THE INVENTION

The present invention concerns a solid support for the solid-phase synthesis of, in particular, peptides or proteins in high yield and in high purity. The support is well suited both to the synthesis of a single peptide or protein and to the parallel and substantially simultaneous synthesis of a plurality thereof. More specifically, the invention relates to a solid support based on a cross-linked polyolefin substrate, especially a cross-linked polyethylene substrate, to which are grafted polymer chains such as polystyrene chains, the polymer chains being functionalized with a chemical functionality facilitating the formation of an anchoring linkage between the polymer moiety and another chemical species, the polymer chains such as polystyrene chains optionally further bearing substituents which are not reactive under the conditions prevailing in the synthesis.

Syntheses employing the substrate of the invention can make use of established chemical methodology, and the substrate is well suited to syntheses on an analytical (microgram) scale or on a preparative (milligram or larger) scale. Furthermore, the substrate of the invention can be employed in both batchwise and continuous-flow procedures which are performed manually, semi-automatically or fully automatically.

In addition, the solid supports of the invention are particularly well suited for use in solid-phase biosystems, notably bioassays, such as immunoassays, DNA hybridization assays or PCR amplification.

BACKGROUND OF THE INVENTION

Until quite recently, solid-phase methods for the synthesis of peptides or proteins have to a large extent been based on the original methodology developed by Merrifield, employing a functionalized cross-linked styrene/divinylbenzene copolymer, the cross-linked copolymer having been formed by the polymerization of styrene monomer to which has been added a few per cent (typically about 2%) of divinylbenzene. This copolymer is generally provided in the form of beads or particles, often with a dominant particle size of 20–80 μm. The functionalization originally preferred by Merrifield [see e.g. J. Am. Chem. Soc. 85, 2149 (1963)] was a functionalization of the aromatic rings of the copolymer with chloromethyl groups, introduced via reaction of the solid copolymer with $SnCl_4$/chloromethyl methyl ether, although a number of other functionalities, including aminomethyl, α-aminobenzyl and α-amino-4-methylbenzyl, have subsequently been employed. Regardless of its nature, the purpose of the functionality is normally to form an anchoring linkage between the copolymer solid support and the C-terminal of the first amino acid which it is desired to couple to the solid support. Later refinements of the Merrifield methodology have included the further introduction, between a functionality (e.g. one of the above-mentioned functionalities) on the polystyrene chains and the C-terminal of the first amino acid which is to be coupled, of a bifunctional "spacer" or "handle" group whose reactivity is tailored inter alia to meet desired requirements with respect both to the coupling of the first amino acid to the solid support and/or to the ease with which the completed, synthesized peptide or protein chain is cleaved from the solid support. Examples of such spacer groups include the phenylacetamidomethyl (Pam) and the p-alkoxybenzyl ester systems. Barany et al. [Int. J. Peptide Protein Res. 30, 705–739 (1987)] have reviewed the development of solid-phase peptide synthesis methodology from its introduction by Merrifield up to about 1986.

The advances in biotechnology which have been made in the last decade or so, particularly in the area of recombinant DNA, have produced a situation in which vast numbers of new protein sequences with undefined or unknown function and/or unknown biological activity have become available. In this connection, detailed structural analysis by site-directed mutagenesis or similar molecular engineering techniques has provided a useful approach to the study of the roles of amino acid residues in active sites of proteins.

However, specific information concerning biologically active functional subunits (peptides) containing ca. 5–40 amino acid residues is preferably obtained through chemical synthesis. Whilst the chemical methodology which had been developed within the period reviewed by Barany (vide supra) was quite capable of yielding such peptides reliably and in high purity when using the above-outlined "conventional" method of solid-phase peptide synthesis (via a "linear" mode of approach), only one peptide was produced per synthesis.

A greater need than ever thus arose for methods employing a "simultaneous" or "parallel" mode of approach to the synthesis of peptides so that a large number of peptides could be synthesized simultaneously (or substantially simultaneously). These peptides could then be used, for example, to define and map the functional entities of proteins. The obvious advantages of a method permitting the parallel and substantially simultaneous synthesis of a multitude of peptides are the attendant saving in time, and the redundancy of the repetitive labour involved in accomplishing the synthesis of each peptide individually.

In this connection, a basic feature of the solid-phase technique of peptide synthesis is that in each elongation of the peptide chain with a further amino acid, all treatment steps are repetitive of the previous cycle with the possible exception of the amino acid coupling step itself, in which a further amino acid that may or may not be identical with that coupled in the preceding cycle is coupled to the peptide chain. Thus, parallel, substantially simultaneous synthesis of two or more peptides could be achieved by performing in parallel the repetitive steps, such as deprotection, neutralization, and washing, which are common to the parallel syntheses. The major technical difficulty here had been the attainment of compartmentalization of each amino acid coupling step so that cross-contamination did not occur.

Several different methods have been proposed for the substantially simultaneous synthesis of a number of peptides:

One of these methods [Geysen et al., Proc. Natl. Acad. Sci. USA. 81, 3998–4002 (1984) and 82, 178–82 (1985)] was devised for rapid screening of peptide epitopes via ELISA (Enzyme Linked Immunosorbent Assay) in 96-microtiter wells. It utilizes acrylic acid-grafted polyethylene rod-and-96-microtiter wells to immobilize growing peptide chains and to perform the compartmentalized synthesis. However, while highly effective, the method is not applicable on a preparative scale, i.e. to the preparation of milligram quantities.

A second method [Houghten, Proc. Natl. Acad. Sci. USA. 82, 5131–35 (1985)] utilizes a "tea bag" containing the traditionally used polymer beads to compartmentalize the synthesis, portions of peptidyl-resin beads being kept apart in sealed bags of fine-mesh polypropylene net. The latter method is relevant to the preparation of milligram quantities.

A more recent, and highly effective, third method is disclosed in WO 90/02749. The basic method of peptide synthesis disclosed therein uses a polymer substrate—especially a polyethylene substrate—which is preferably in the form of a sheet or film, and to which polystyrene chains have been grafted. The polystyrene chains, which may bear further substituents which are not reactive under the conditions prevailing in the synthesis, have an estimated peak molecular weight (not including optional substituents) of at least 200,000, and at least part of the grafted polystyrene chains are functionalized with a chemical functionality which facilitates the formation of an anchoring linkage between the polystyrene moiety and an at least N-protected and optionally carboxyl terminal derivatized amino acid.

Very high loading with synthesized peptide can be achieved with a polystyrene-grafted polymer substrate as disclosed in WO 90/02749, and when in the preferred form of a sheet or film, such a polystyrene-grafted polymer substrate is particularly convenient for the purposes of parallel synthesis of multiple peptides. Thus, for example, it is easy to cut a sheet or film into pieces of any desired size and/or shape and to transfer such pieces, if appropriate, from one reaction vessel to another; furthermore, a material in the form of a sheet or film is easy to mark for identification purposes (e.g. in connection with the latter mentioned transfer between various reaction vessels).

Thus, when the invention disclosed in WO 90/02749 is employed in the context of parallel and substantially simultaneous synthesis of a plurality of peptides, an appropriate plurality of essentially identical substrates of the above-described type are provided, after which the synthesis proceeds as follows:

a) the members of the plurality of polystyrene-grafted polymer substrates are optionally physically segregated into two or more sets each comprising one or more members of the plurality;

b) an N-protected and optionally carboxyl terminal derivatized amino acid is coupled to the functionalized polystyrene moieties of each member of the plurality or, where applicable, each member of each set, the N-protected and optionally carboxyl terminal derivatized amino acid employed being identical for all the members of the plurality or, where applicable, all the members of one set, and, where applicable, further being in accordance with one of the following alternatives:
(i) identical for all the sets,
(ii) when the number of said sets is greater than two, identical for at least two of the sets,
(iii) different for each set,
the functionality and the N-protected and optionally carboxyl terminal derivatized amino acid being adapted to each other such that the anchoring linkage formed can subsequently be cleaved substantially without degradation of the peptide or protein chain which is to be synthesized;

c) each member of the plurality or, where applicable, each member of each set is treated so as to remove the N-protecting group from an N-protected amino or substituted amino group of the coupled and N-protected amino acid, such that reaction of the amino or substituted amino group of the coupled amino acid with a carboxyl group or an activated carboxyl group of a further N-protected amino acid is facilitated;

d) the amino or substituted amino group of the amino acid last coupled to the functionalized polystyrene moieties of each member of the plurality or, where applicable, of each member of each set is reacted with a carboxyl group or an activated carboxyl group of a further N-protected amino acid, so as to form a peptide bond between the amino or substituted amino group and the carboxyl group or activated carboxyl group, the further N-protected amino acid being identical for all the members of the plurality or, where applicable, all the members of one set, and, where applicable, further being in accordance with one of the three alternatives mentioned above in connection with step b);

e) each member of the plurality or, where applicable, each member of each set is optionally treated so as to remove the N-protecting group from an N-protected amino or substituted amino group of the last-coupled N-protected amino acid, such that reaction of the amino or substituted amino group of the latter amino acid with a carboxyl group or activated carboxyl group of a further N-protected amino acid is facilitated;

f) in those cases where step e) has been performed, steps d) and e) are repeated a desired number of times;

g) each member of the plurality or, where applicable, each member of each set is optionally treated so as to remove some or all protecting groups possibly remaining on the amino acid moieties of the synthesized peptide or protein chain;

h) each member of the plurality or, where applicable, each member of each set is optionally treated so as to cleave the linkage anchoring the synthesized peptide or protein chain to the functionalized polystyrene moieties of each member of the plurality or, where applicable, of each member of each set; and, i) if appropriate, any further undesired group is removed from a synthesized peptide or protein chain.

The methodology disclosed in WO 90/02749 is equally applicable to the synthesis of a single peptide or protein. In this case only one polystyrene-grafted polymer substrate of the type in question is used, and the alternatives mentioned under b) and f), above, do not then apply; apart from this, the steps in the process are entirely analogous to those recited above.

It is also appropriate to mention here another document, viz WO 91/13098. This document discloses solid supports which are very closely related to the polystyrene-grafted substrates of WO 90/02749 and which are suited for use in solid-phase biosystems, such as bioassays, e.g. immunoassays. The solid supports of WO 91/13098 differ from those of WO 90/02749 only in that they are functionalized with chemical functionalities from which a peptide which has been attached thereto, or a peptide which has been synthesized thereon (e.g. in the manner disclosed in WO 90/02749), will not become detached under any normally applying chemical or physical conditions.

After a number of years of experience in the handling and use of the inventions described in WO 90/02749 and WO 91/13098, it has become apparent that although the substrate/support materials disclosed therein offer a number of significant advantages in relation to the state of the known art at the time of filing of the respective PCT applications, it would nevertheless be advantageous to be able to improve the properties of the materials in certain respects.

Thus, for example, it became clear that the occlusion, in the PE film material, of polystyrene homopolymer during the grafting process led to undesirable inhomogeneity of the grafted material owing to the formation of small bubbles or blisters in the material. Apart from the fact that it is necessary to carry out a time-consuming extraction of this occluded homopolymer from the PS-grafted PE film in order to obtain a material with satisfactorily reproducible chemical and physical behaviour in the context of applications to synthesis, the inhomogeneity due to the above-mentioned bubbles/blisters results in the optical properties (e.g. clarity, light transmission and reflecting properties) of the PS-grafted PE-material being considerably poorer than could be desired.

It has also been found that, for example, at high levels of loading of synthesized peptide or protein on the PS-grafted PE substrates of WO 90/02749, the mechanical properties of the material deteriorate, leading to a tendency for the material to fragment in an uncontrolled fashion.

Furthermore, the thermal and other properties of the PS-grafted PE substrates of WO 90/02749 impose limits on the nature of the functionalities which can be introduced into the polystyrene part of the material, and on the conditions under which the materials in question can be used (thus, for example, the PS-grafted PE material of WO 90/02749 dissolves in solvents such as xylenes at 100° C.). The ability to be able to withstand functionalisation conditions entailing, for example, the use of highly "aggressive" organic solvents (such as xylenes) and relatively high temperatures would permit functionalisation with a range of functionalities which could considerably broaden the synthetic applicability of the substrate material, and would therefore constitute a highly desirable improvement of the material.

Moreover, in continuing investigations of the applicability of the substrates disclosed in WO 91/13098 (vide supra) for use in solid-phase biosystems, such as bioassays, e.g. immunoassays, it became more and more clear that the lack of hydrophilicity of the material imposed limits on its breadth of applicability in connection with, for example, assays of the ELISA type. It thus became apparent that a material of the general type in question but having significantly improved hydrophilic properties would have considerable advantages.

BRIEF DISCLOSURE OF THE INVENTION

The present invention provides a material which to a great extent meets the requirements discussed above. Thus, it has surprisingly been found that a polyolefin, notably polyethylene, which has been subjected to a treatment leading to cross-linkage of the polyolefin (e.g. a treatment such as irradiation with high energy electrons or γ radiation, or possibly treatment with a peroxide, e.g. an organic peroxide such as benzoyl peroxide) can lead to a material which can subsequently undergo grafting with polymer, such as organic polymer, chains such as polystyrene chains, in the same manner as described in WO 90/02749, to give a grafted material which, for example:

(i) still possesses excellent mechanical and optical properties, (ii) can withstand harsher chemical/physical conditions (e.g. higher temperatures, aggressive solvents) than the material of WO 90/02749, (iii) retains all the advantages of the material of WO 90/02749 with respect to, e.g., peptide synthesis, and (iv) can be further modified by functionalisation or derivatization with appropriate substituent groups so as to acquire a high degree of hydrophilicity while at the same time being compatible with synthetically relevant organic solvents and retaining good optical and mechanical properties.

Thus, solid supports of the present invention can, for example, be employed in a method completely analogous to that disclosed in WO 90/02749 to provide—on both an analytical and a preparative scale-desired peptides or proteins in high yield and high purity, (e.g. in connection with studies in structure-activity relationships, investigations such as mapping of antigenic epitopes, determination of details of hormone-receptor interactions and screening for pharmacologically active peptidyl drugs).

It is envisaged that the grafted cross-linked polyolefin substrates according to the invention, including hydrophilic versions thereof, comprising linker or spacer groups adapted to the particular chemistry in question may be valuable in the solid-phase synthesis of single or multiple polymer or biopolymer molecules other than peptides and proteins. Examples would include analogues of oligopeptides, polypeptides, proteins, polyamides, and polyamino acids, e.g., depsipeptides, entothiopeptides, thiomethylene analogues, reduced peptide bond analogues, ketomethylene analogues, hydroxymethylene analogues, retro-inverso analogues and peptides containing other peptide bond surrogates, lipopeptides, dehydro analogs, sulfated peptides, phosphorylated peptides, glycosylated peptides, cyclic peptides, peptides containing methylated (and otherwise alkylated) peptide bonds, peptides containing alfa,alfa-disubstituted amino acids, peptides containing non-proteinogenic amino acids, multiple antigen peptide systems (MAPS) [Tam, Proc. Natl. Acad. Sci. USA, 85, 5409 (1988)], peptoids [Simon et al., Proc. Natl. Acad. Sci. USA, 89, 9376 (1992)], pyrrolinone-based peptidomimetics [Smith et al., J. Am. Chem. Sci. USA, 89, 114, 10672 (1992)] and other peptide mimetics and peptide mimics. Further examples would include the synthesis of oligonucleotides, polynucleotides, nucleic acids (DNA, RNA) and analogues thereof, e.g., mono- [Stech et al., J. Am. Chem. Soc., 106, 6077 (1984) and Conolly et al., Biochemistry, 23, 3443 (1984)], dithiophosphates [Nielsen et al, Tetrahedron Lett., 29, 2911 (1988)], methylphosphonates [Löscher and Engels, Nucleosides Nucleotides, 7, 729, (1988)], borano phosphates [Sood et al., J. Am. Chem. Soc., 112, 9000 (1990), etc. [Uhlmann and Peyman, Chem. Rev., 90, 544 (1990)], formacetal analogues [Matteucci, Tetrahedron Lett., 31, 2385 (1990)], carbamate analogues [Coull et al., Tetrahedron Lett., 28, 745, (1987) and Stirchak et al., J. Org. Chem., 52, 4202 (1987)], siloxane analogues [Cormier et al., Nucleic Acids Res., 4583 (1988)], or dimethylenethio-, sulfoxido-, and sulfono-linked analogues [Huang et al., J. Org. Chem., 56, 3869 and Schneider and Benner [Tetrahedron Lett., 31, 335 (1990)], or circular oligonucleotides [Prakash and Kool, J. Chem. Soc., Chem. Commun., 1161 (1991)], morpholino-type backbone analogues [Stirchack et al., Nucleic Acids Res., 17, 6129 (1989)], peptide-backbone analogues [Tyaglov et al., Zh. Obshch. Khim., 57, 2124 (1987), Takemoto and Inaki, Polym. Mat. Sci. Eng., 58, 250 (1988)], including peptide nucleic acids (PNA) [Nielsen et al., Science, 254, 1947 (1991)]; Egholm et al., J. Am. Chem. Soc., 114, 1895 (1992) and J. Am. Chem. Soc., 114, 9677 (1992)]. Examples would also include the synthesis of oligosaccharides, polysaccharides, sugars and analogues thereof [Danishefsky et al., Science, 260, 1307 (1993)]. Finally, the synthesis of chimeric conjugates in any combination of the above-mentioned molecules can be envisaged.

As a further aspect of the invention, the grafted cross-linked polyolefin substrates, including hydrophilic versions, can be used to generate so-called libraries, e.g., synthetic peptide combinatorial libraries [Houghten et al., Nature 354, 84 (1991)], which consist of tens of millions of individual peptides, allowing for the rapid screening for biologically active peptides in various assay systems. The libraries may, for example, be prepared in the way analogous to that recently described [Eichler and Houghten, in "Peptides 1992", C. H. Schneider and A. N. Eberle, eds., 1993, Escom Science publishers B.V., pp. 320–321] employing another contiguous support, namely the cotton carrier [Eichler et al., Pept. Res. 4, 296 (1991)].

In another aspect, it is envisaged that grafted cross-linked polyolefin substrates, including hydrophilic versions, may be valuable in the solid-phase synthesis of single or multiple nonpolymeric molecules. Examples would include the synthesis of organic molecules, e.g. a variety of therapeutic agents such as derivatives of 1,4-benzodiazepines Ellman et al., J. Am. Chem. Soc. 114, 10997 (1992)].

In another line of approach, the present invention pertains to the advantageous use of grafted cross-linked polyolefin substrates, including hydrophilic versions, on which peptides or other molecular species have been bound or synthesized directly, in solid-phase biochemistry [see, e.g., "Solid-Phase Biochemistry—Analytical and Synthetic Aspects"; W. H. Scouten, ed., John Wiley & Sons, New York, 1983], notably solid-phase biosystems, especially bioassays or solid-phase techniques which concern, for example, diagnostic detection/quantitation (such as ELISA and related technologies) or affinity purification of peptides and proteins, e.g., antigens, immunogens, enzymes, antibodies, receptors, hormones, as well as other biomolecules, including saccharides, lipids and nucleic acids [see, e.g., "Affinity Chromatography—A Practical Approach", P. D. G. Dean, W. S. Johnson and F. A. Middle, eds. IRL Press Ltd., Oxford, 1986; "Nucleic Acid Hybridization—A Practical Approach", B. D. Harnes and S. J. Higgins, IRL Press Ltd., Oxford, 1987]. Some recent solid-phase biochemistry techniques of particular interest include VLSIPS (a technology combining solid-phase synthesis with photolithography) [Fodor et al., Science 251, 767 (1991)] and immuno-PCR [Sano et al., Science 258, 120 (1992)].

It is further envisaged that grafted cross-linked polyolefin substrates, including hydrophilic versions, may be valuable as aids in general organic chemistry, analytical chemistry, environmental chemistry and related areas of chemistry. Examples would include polymer-bound reagents, ion exchangers, polymer-bound catalysts and polymer-bound species capable of binding metal ions (selectively), e.g., cryptands or crown-ethers, chelating groups, and antibodies, such as monoclonal antibodies specific for mercury ions [Wylie et al., Proc. Natl. Acad. Sci. USA 89, 4104 (1992)], and other ions. Examples would also include the immobilization of metal reagents [J. Chem. Soc. Perkin Trans I, 3165 (1992)] and other reagents to simplify recovery and recycling.

The cross-linking of the polyethylene prior to the grafting process leads to significant improvement in the quality of the grafted specimens.

In the grafting with styrene, the high level of grafting achievable on uncross-linked polyethylene specimens is ensured in the styrene/methanol mixture by a constant (low) level of swelling throughout the grafting process. However, small inhomogeneities in the swelling can be amplified during the grafting process and lead to inhomogeneities in the grafting and at higher graft levels to the formation of large amounts of occluded polystyrene (homopolymer) and bubble formation. By choice of solvent, the formation of such inhomogeneities can only be avoided if the methanol styrene mixture can be tuned to be an equally good (actually equally poor) solvent for all composition ratios of polyethylene and polystyrene.

It is possible to envisage several mechanisms through which the radiation induced cross-linking of the polyethylene prior to grafting can contribute to ensure the formation of homogeneous grafting.

The cross-linking will reduce (slightly; dependent on dose) the crystallinity of the polyethylene. The crystallites act in the uncross-linked material as large physical cross-links that prevent the material from dissolving under the conditions of the grafting process. However, crystallites do not swell and act as such as inhomogeneities in the material.

The cross-links will reduce the equilibrium swelling (in fact, measurement of equilibrium swelling is a classic method to characterize the number of cross-links in a polymer network). Especially important in this context is the fact that the cross-links will add an elastic part to the free energy of swelling. This means that high degrees of swelling in certain areas of the specimen become unfavourable, whereas in the uncross-linked case they may act as sites of instabilities in the composition.

In was not a priori clear that the combination of these effects (and possibly others) almost totally suppresses the formation of occluded (homo)polystyrene. From a production point of view, this is very important because it means that the relatively tedious extraction procedures needed to remove the occluded polymer can be avoided.

Figure 1A:
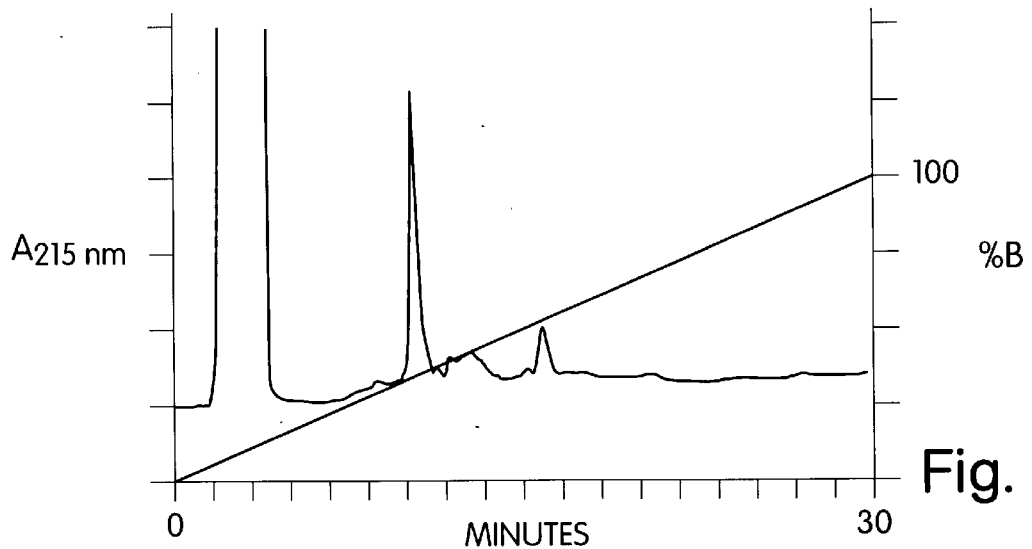
FIG. 1. Analytical HPLC chromatograms of crude human gelsolin fragment 160–169, i.e. H-Gln-Arg-Leu-Phe-Gln-Val-Lys-Gly-Arg-Arg-NH$_2$, synthesized on: (A) the Boc-BHA derivatized PS-grafted XLPE film prepared according to Example 3(b) herein; (B) the Boc-BHA/PEO-film prepared according to Example 4(d); and (C) the Boc-BHA/AM-film prepared according to Example 4(c) herein. A μBONDAPAK™ C$_{18}$ (Waters) reverse-phase column (5 μm, 0.46×30 cm) was employed; buffer A was 5% v/v acetonitrile in water containing 445 μl of TFA per liter, and buffer B was 60% v/v acetonitrile in water containing 390 μl of TFA per liter. The flow rate was 1.5 ml/min, and the linear gradient employed was 0–100% of buffer B in 30 min. The eluents were monitored spectrophotometrically at 215 nm.

buffer A was 5% v/v acetonitrile in water containing 445 μl of TFA per liter, and buffer B was 60% v/v acetonitrile in water containing 390 μl of TFA per liter. The flow rate was 1 ml/min, and the linear gradient employed was 0–100% of buffer B in 30 min. The eluents were monitored spectrophotometrically at 215 nm. Temperature 40° C.

DETAILED DESCRIPTION OF THE INVENTION

In one aspect, the invention relates to a cross-linked polyolefin substrate grafted with polymer chains, at least part of the polymer chains of the polymer-grafted substrate being functionalized with a chemical functionality facilitating the formation of an anchoring linkage between the polymer moiety and another chemical species. In important embodiments of the invention, the chemical functionality is a functionality facilitating the formation of an anchoring linkage between the polymer moiety and an at least N-protected and optionally carboxyl terminal derivatized amino acid.

A most important polymer with which the cross-linked polyolefin is grafted is polystyrene, and hence, a most important embodiment of the invention is a cross-linked polyolefin substrate grafted with polystyrene chains, said polystyrene chains optionally further bearing substituents which are not reactive under the conditions prevailing in peptide synthesis, at least part of the polystyrene chains of the polystyrene-grafted substrate being functionalized with a chemical functionality facilitating the formation of an anchoring linkage between the polystyrene moiety and an at least N-protected and optionally carboxyl terminal derivatized amino acid.

In the following detailed description, the embodiment using polystyrene as the polymer is the embodiment particularly discussed, but it will be understood that also a large number of other suitable polymers can be used analogously to polystrene or with modifications which will be evident to the person skilled in the art, and with the same advantages as mentioned above compared to grafting of non-cross-linked polyolefin. Thus, one can envision new materials based on cross-linked polyolefin such as polyethylene or polypropylene, grafted with one or combinations of the following monomers to give polymer or copolymer grafts which can be functionalized easily with suitable chemical handles for use as solid phase carriers. There are two general methods for functionalization of the polymer material. One is by chemical modification of the polymer backbone, the other is to use monomers with masked or unmasked chemical reactive functionalities. Apart from styrene and styrene derivatives, acrylates are considered the most interesting monomers. Maleic anhydride and its derivatives are interesting because of the possibility of alternating copolymers with styrene. Vinyl acetate is interesting because of the broad spectrum of applications polyvinyl alcohol grafts possess. PVAL grafts offer the possibility of many chemical modifications.

In the following, various alternative monomers are listed; wherever the monomers are hydrophilic, this is indicated with a #:

Acrylic Monomers
  Acrylic Acid and Salts and Esters Thereof (#)
    The carboxylic acid group of polyacrylic acid is a suitable functionality for many purposes. The carboxylic acid can be derivatized by reaction with e.g. amines or alcohols.
  Acrylamides (#)
    The amide groups can be partly hydrolyzed to give carboxylic acid.
  Acrylonitrile (#)
    Acrylonitrile can be partly hydrolyzed to give carboxylic acid groups. Acrylonitrile can also be derivatized by electrophilic reactions on the cyano group.
  Methyl Methacrylate
    The ester group can be hydrolyzed to give a carboxylic acid or reacted with e.g. amines or alcohols to give amides and ester.
    Methyl methacrylate offers the possibility of an alternating copolymer with styrene.
  2-Hydroxyethyl Methacrylate (HEMA) (#)
    The free alcohol can directly be derivatized through e.g. an ether or ester functionality or be oxidized to either a reactive aldehyde or a carboxylic acid.
  Glycidyl Acrylate (#)
    The glycidyl ("epoxy") functionality can be reacted with e.g. amines, alcohols or sulfides to give amines, ethers and thioethers, or the glycidyl group can be hydrolyzed to give a 1.2 dialcohol suitable for reaction with e.g. aldehydes giving an acetal.
  Examples of Other Hydrophilic Acrylic Monomers of Potential Interest (#)
    Acrylochloride, 2-hydroxyethylacrylate, 2-hydroxypropylacrylate, methacrylic acid, N,N-diethylacrylamide, N-methyl acrylamide, 2.3-dihydroaxypropyl methacrylate, 2-dimethylaminoethylmethacrylate, polyethylene glycol monomethacrylate and polyethylene glycol monomethylether monomethacrylate.
Maleic Acid Derivates
  Maleic Anhydride
    E.g. as a copolymer with styrene to give a poly(styrene-co-malic anhydride), which can be functionalized by reaction with e.g. a mono-Boc diamine or a diamine, which after deprotection of the Boc group will give an aminofunctionalized polymer. Maleic anhydride shows strong tendency to alternation in copolymerization with styrene. N-alkyl or aryl-maleimides possesses the same potentials as monomers for copolymerization with styrene.
  Vinyl Acetate
    Hydrolysis gives polyvinyl alcohol (PVAL), which can easily be derivatized by reaction with e.g. acids, tosylates, ketone or aldehydes to give esters, ethers, ketals or acetals.
Other Monomers
  4-Vinylpyridene
    The heterocyclic nucleus can be derivatized by e.g. electrophilic substitution, e.g. formylation or nitration, N-vinylpyrrolidon, vinylsulfone, vinylsulfonic acid, 4-vinylbenzyldimethylamine, polyethylene glycol, monomethacrylate, monoacrylate Suitable methods of cross-linking are irradiation with high-energy electrons or γ radiation, although for some polyolefins, such as polypropylene, a radical cross-linking process involving the use of e.g. a peroxide species will often be the preferred process.

The polyolefin substrate may be fashioned in any suitable form, for example a sheet, film, bead, pellet, disc, ring, tube, rod, net, tray, microtiter plate, or multi-bladed stick (such as a multi-bladed stick in the form of an "immuno-stick", or a functional equivalent thereof, as used in certain types of immunochemical assay procedure). In preferred embodiments of the substrate of the invention, the polyolefin from which the cross-linked polyolefin is prepared is polyethylene, very suitably low-density polyethylene, although high-density polyethylene is also believed to be suitable.

One particularly useful form of the substrate of the invention is a sheet or film.

Polystyrene chains grafted to the cross-linked polyolefin may be chains of polystyrene itself or of polystyrene which has been substituted to some extent with substituents which are not capable of reaction under the conditions prevailing in the synthesis. Such substituents may suitably be, for example, alkyl substituents, such as methyl, ethyl, propyl or butyl, alkoxy substituents, such as methoxy, ethoxy, propoxy and butoxy, or aryloxy substituents, such as phenoxy. The substitution will preferably take the form of substitution in the aromatic rings by one or more substituents, e.g. one or more of the above-mentioned substituents, although substitution at non-aromatic carbon atoms of vinyl group origin may also be envisaged.

A particularly interesting type of further substituent on the polymer chains such as polystyrene chains is a substituent which is such that the polymer-grafted cross-linked polyolefin substrate is thereby rendered swellable by water or aqueous media, which is especially desirable when applying a substrate of the invention to an assay employing an aqueous medium, e.g. an immunoassay such as an ELISA assay.

The substituents which are such that the polymer-grafted cross-linked polyolefin substrate is thereby rendered swellable by water or aqueous media may, e.g. be selected from the group consisting of polyoxyethylene and oligooxy-ethylene moieties, polyacrylamides and oligoacrylamides, polyamides and oligoamides, saccharides, including dextrans, cellulose, agarose, starch, and agar, peptides, amino acids, polycations, polyanions, polyisothiocyanates, and hydrophilic natural substances.

As interesting examples, such substituents may suitably be derived from e.g. polyoxyethylene-containing species, such as 3,6,9-trioxadecanoic acid. Thus, e.g. 3,6,9-trioxa-decanoyl groups are e.g. suited, as disclosed herein. Further suitable groups include substituents derived from N,N-dimethylacrylamide, such as 2-(N,N-dimethylcarbamyl) ethyl groups, as exemplified further herein, below.

In certain preferred embodiments of substrates according to the present invention, namely in embodiments in which there is no particular requirement of hydrophilicity of the substrate, the grafted polystyrene chains are chains of non-substituted polystyrene.

As in the case of the substrates according to WO 90/02749, it appears to be particularly advantageous that the polystyrene chains grafted to the cross-linked polyolefin substrate are of an estimated peak molecular weight, not including optional substituents present on the polystyrene chains, of at least 200,000. Polystyrene chains fulfilling this condition may suitably be formed, as in WO 90/02749, by a substantially radical-initiated reaction (brought about, for example, by relatively low-dose γ irradiation) between the cross-linked polyolefin substrate and optionally substituted styrene monomer present in a solution of the monomer in an organic solvent.

With regard to the chain length (chain molecular weight) of the grafted polystyrene chains, all indications are that this can be varied in the same manner as described in WO 90/02749, i.e. by varying the composition of the solution of styrene (or substituted styrene) monomer which is used for grafting. Thus, in this connection, for example, and by analogy with the results described in WO 90/02749, a solution of composition 70:30 (v/v) methanol/styrene (or of a composition in the region thereof) seems to be very suitable for achieving grafting of suitably long chains of polystyrene to a cross-linked polyethylene substrate.

It should be pointed out here, as is further discussed below, that grafting of polystyrene chains to the preferred cross-linked polyolefin, i.e. cross-linked polyethylene (XLPE), does not appear to result in occlusion of polystyrene homopolymer in the XLPE, and for this reason no extraction of the PS-grafted material is necessary. Thus, it is not possible to arrive at an estimate of the peak molecular weight of the grafted chains in the manner employed in WO 90/02749, i.e. by assuming that the length (or rather the distribution of chain molecular weights) of homopolymeric polystyrene chains which are not grafted to, but become occluded into, the PE material will reflect that of the grafted chains formed under the same conditions.

Since no occluded homopolymer is formed in the case of the present substrates, and since the cross-linked polyolefin is insoluble in all available solvents, it is not possible to estimate peak molecular weights of grafted PS chains in the ways discussed in WO 90/02749. However, the close relationship of the underlying polymer materials employed in the preferred embodiments of the present invention and of the invention described in WO 90/02749, and the use of the same approach to the grafting of PS chains onto the underlying material, make it reasonable to conclude that the distribution of grafted polystyrene chain lengths obtained under a given set of conditions using, for example, XLPE as the cross-linked polyolefin will closely resemble that obtained under the same conditions using non-cross linked polyethylene (as in WO 90/02749). For this reason it is believed that chain molecular weight criteria which apply in the case of the invention disclosed in WO 90/02749 also apply in the case of the present invention, and that effects deriving from the magnitude of the estimated peak molecular weight in the substrates of WO 90/02749 also apply in the present context.

Thus, as in WO 90/02749, it may be concluded that when long, grafted polystyrene chains formed in the context of the present invention are functionalized, they may be presumed—in the same way as discussed in WO 90/02749—to behave, with regard to their reactivity towards dissolved reagents, to a large extent as though they were non-grafted (i.e. free) functionalized polystyrene chains in homogeneous solution.

Further, as in WO 90/02749, it is preferred in the context of the present invention that the estimated peak molecular weight of the polystyrene chains grafted to the polymer, not including optional substituents, is in the range of 300,000–1,600,000, in particular 400,000–1,400,000, preferably 600,000–1,200,000. A very suitable estimated peak molecular weight of the polystyrene chains is 700,000–1,000,000. It is believed that the higher estimated peak molecular weights of 400,000 and above are particularly advantageous.

The degree of polystyrene chain grafting of the cross-linked polyolefin substrate, that is, the weight percentage of polystyrene relative to the cross-linked polyolefin substrate, depends, of course, on the length of the polystyrene chains, the grafting site density and the dimensions of the substrate, and may vary within wide limits. Thus, in the case of, e.g., a sheet or film of cross-linked polyolefin substrate of thickness in the range of 25 to 100 μm, the degree of polystyrene chain grafting may be, e.g., from about 5 to about 800% by weight, such as from about 10% to about 700%. Both very low and very high degrees of polystyrene chain grafting, as well as intermediate degrees of grafting, are of value in the context of preferred embodiments of the present invention.

Thus, for analytical purposes, where it is normally desired to be able to synthesize peptide sequences of proteins on a small scale, typically microgram scale, the provision, for example, of a cross-linked polyolefin substrate with a relatively low degree of polystyrene chain grafting, such as, e.g. 5 to 200%, or even 10 to 60% (for a sheet or film of cross-linked polyolefin substrate of thickness in the range of 25 to 100 µm), and preferably with a controlled, often low extent of functionalization, ensures controlled limitation of the amount(s) of peptide(s) formed.

Polystyrene-grafted XLPE sheet or film of the present invention is particularly advantageous with respect to analytical aspects of peptide chemistry or biochemistry in that its excellent transparency to light, particularly visible light, and its homogeneity (both of which are, as mentioned above, superior to those of the PS-grafted material according to WO 90/02749), makes it ideal for use in conjunction with spectrophotometric techniques, e.g. for the monitoring (for example by an ELISA technique) of antigen/antibody reactions which can be monitored by a subsequent colour reaction and in which the antigen may be a particular peptide sequence synthesized on and remaining anchored to the solid support.

For preparative purposes, where the attainment of the highest possible yield of a peptide or protein is clearly desirable, it is advantageous to use the highest practicable degree of grafting. From an overall point of view, the practical upper limit of the degree of grafting for a sheet or film of cross-linked polyolefin substrate of thickness in the range of 25 to 100 µm (as employed according to preferred embodiments) will often be about 500–600% by weight, although special applications may make it desirable to exceed this range, such as to a degree of grafting of about 700%. On the other hand, the lowest degrees of grafting practicable will normally not be below about 40% for such a thin sheet or film. For most practical purposes, the degree of grafting of such a thin sheet or film will be in the range of about 100–600% and will often be in the range of 200–600% and, for preparative purposes, often preferably 200–400% by weight, which seems to be a suitable range both from the point of view of the yield and efficiency of peptide syntheses performed using functionalized, grafted sheet.

As will be apparent from the examples illustrating the present invention, excellent yields of highly pure peptides are—as in the case of the invention disclosed in WO 90/02749—obtainable.

As mentioned above, the polystyrene-grafted cross-linked polyolefin substrate is formed by a substantially radical-initiated reaction between the substrate and optionally substituted styrene monomer present in a solution of said monomer in an organic solvent. For reasons discussed in WO 90/02749, it appears to be advantageous, from the point of view of obtaining long, substantially non-cross-linked polystyrene chains, to perform the grafting in a solvent in which the growing polystyrene chains are poorly swelled or solvated, such as a hydroxylic organic solvent, in particular an alcohol. Preferred alcohols for this purpose are $C_{1-4}$ aliphatic alcohols. In practice, methanol has been found to be a most suitable solvent, but other alcohols may be suitable candidates, e.g. ethanol, propyl or isopropyl alcohols, or even n-butyl, iso-butyl, sec-butyl or tert-butyl alcohols.

The volume percentage (% v/v) of optionally substituted styrene in the solution used for the grafting, such as a solution in a solvent which swells or solvates the growing polystyrene chains poorly, e.g. a hydroxylic solvent as explained above, in particular an alcohol as explained above, such as, e.g., methanol, has a marked influence on the molecular weight of the grafted polystyrene chains formed, in that, at least up to a certain point, the chain-length-increasing effect of the solvent is greater, the greater the volume percentage of the solvent in the solution. Thus, while the volume percentage of optionally substituted styrene in the solution may be within a very broad range, such as between 1 and 95%, this volume percentage will normally be in the range of 10 to 90%, more usually 20 to 80%. A very interesting range for the volume percentage of the optionally substituted styrene in the solution is between 25 and 50%, and as will appear from the examples, about 30% by volume has been found in practice to give supports with excellent properties. However, it is possible that the optimum solvent composition in the context of the present invention may deviate somewhat from the value of about 30% styrene monomer found in connection with the grafting process in WO 90/02749. Thus, owing to the fact that in order to swell satisfactorily, the cross-linked amorphous phase of XLPE is believed to require a higher percentage of styrene than is the case for the PE material employed in WO 90/02749, it is likely that solutions containing slightly more than 30% of styrene monomer, e.g. in the range of 30–35%, may prove to be optimal, at least for XLPE, in the present context.

The grafting process is very suitably performed by γ-irradiation, and is then suitably performed at a dose rate in the range of from about 1 to about 100,000 Gy/hour, in particular about 200–5000 Gy/hour, such as about 300–1000 Gy/hour. It is believed that the intensity of the irradiation is of considerable importance to the obtainment of the desirable configuration with long, substantially non-cross-linked polystyrene chains; if the intensity is too high, the free radical formation will be so high that the grafting will tend to involve a greater number of shorter chains and perhaps a higher degree of chain cross-linking, both of which are normally not desired.

On the whole, the optimization of chain length and grafting is achieved via the choice of reaction mixture, radiation dose-rate, and temperature during irradiation.

While the above-described method involving γ-irradiation is the presently preferred method, it is believed that polystyrene-grafted substrates and substrates grafted with other polymers may suitably be prepared using a different strategy involving conventional radical initiators, such as peroxides, for example hydrogen peroxide, benzoyl peroxide or diacetyl peroxide, or azo compounds as the radical-forming principles. Other radical-forming principles which may be employed are, e.g., ozone and UV-radiation; another possibility is an electron beam (although of considerably lower energy than employed, e.g., for cross-linking a polyolefin substrate). The important thing is that the method used for the radical generation be one which is suitable for relatively well-controlled radical-initiated growth of the polystyrene chains. It is believed that the conditions mentioned above concerning the importance of the properties of the solvent used also apply in connection with these free radical initiation principles.

While the polymer-grafted cross-linked polyolefin substrate may be in any suitable form, such as explained above, very interesting embodiments of the invention are such in which it takes the form of a sheet or film. The thickness of the cross-linked polyolefin substrate itself, for example an XLPE substrate, which is the starting material for such a sheet or film, may vary within a wide range and will normally be from 10 to 10,000 µm, for most purposes preferably in the range 25 to 1000 µm, and typically in the range 25 to 100 μm such as 25 to 75 μm. The grafting process leads, of course, to an increase in the total thickness. Thus, the thinner a sheet or film, the greater will the percentage increase in thickness be for a given set of grafting conditions. As an example, a thin grafted sheet or film may have a thickness in the range of 25 to 200 μm.

A sheet or film has, as discussed in WO 90/02749, a number of advantages in the practical performance of, for example, peptide or protein synthesis. Thus, e.g., sheet or film may easily be cut out in suitable sizes for arranging in the reaction vessels used, such as any type of known solid-phase peptide synthesis reaction vessels, including flasks, beakers, microbeakers, funnels, wells, columns or nets.

The film or sheet support makes it possible, as also discussed in WO 90/02749, to devise new practical ways of handling the peptide synthesis. Thus, e.g., a number of sheet or film pieces may be arranged on a common support and thus be kept together during the various stages of peptide synthesis, e.g. by being exposed together to the various reagents and washing solvents, or the pieces may be arranged in sets, each set being subjected to a particular combination of reaction media.

This latter possibility facilitates efficient "compartmentalization" whereby two or more peptides can be prepared in a parallel and substantially simultaneous manner, this has already been described in detail, above. One practical way of handling the polymer support in the form of a sheet or film for compartmentalization purposes is to cut the sheet or film into a desired number of pieces which are then marked indelibly, e.g. by means of graphite-based ink melted into the surface of some part of the sheet or film. Another possibility is to have the various pieces present on one and the same large piece of sheet or film and then treat the different areas (which are suitably marked as described above) jointly or separately as the case may be. Evidently, one embodiment is to allow the pieces to remain on one and the same film as long as the treatments to be performed are the same, and then divide the film into sub-units when the steps to be performed are different.

The chemical functionality facilitating the formation of an anchoring linkage between an at least N-protected and optionally derivatized amino acid and the functionalized polystyrene moiety is suitably a member of, or is derived from a member of the group comprising:

chloro-, bromo- and iodo-substituted alkyl, amino-substituted alkyl, amino- and aryl-substituted alkyl, amino- and alkylaryl-substituted alkyl, hydroxy-substituted alkyl.

The functionality, if derived from any of said group, may be a functionality with a spacer group such that a synthesized peptide or protein chain will be cleavable from the polystyrene moiety substantially without degradation of said chain.

According to suitable embodiments of the invention, chloro-substituted alkyl is chloromethyl, amino-substituted alkyl is aminomethyl, amino- and alkyl-substituted aryl is α-aminobenzyl (benzhydrylamino), amino- and alkylaryl-substituted alkyl is selected from the group consisting of α-amino-2-, α-amino-3- and α-amino-4-methylbenzyl (the latter also being known as 4-methylbenzhydrylamino), and hydroxy-substituted alkyl is hydroxymethyl.

Concerning the initial functionalization of the polystyrene-grafted cross-linked polyolefin substrate, more than fifty methods have been described in connection with traditional solid-phase peptide synthesis (see Barany and Merrifield in *The Peptides*. Vol. 2, Academic Press, New York, 1979, pp. 1–284, and Stewart and Young, *Solid Phase Peptide Synthesis* 2nd Ed., Pierce Chemical Company, Illinois, 1984), of which reactions for the introduction of chloromethyl (via a chloromethyl methyl ether/$SnCl_4$ reaction, aminomethyl (via a N-hydroxymethylphthalimide reaction; see Mitchell et al., *Tetrahedron Lett.*, 3795, (1976)) and benzhydrylamine (Pietta and Marshall, *J. Chem. Soc.*, 650 (1970)) groups are the most widely applied. Other reactive functionalities which have been initially introduced include 4-methylbenzhydrylamine and 4-methoxybenzhydrylamine. All of these established methods are in principle useful within the context of the present invention. Preferred embodiments within the context of the present invention employ aminomethyl as the initial functionality, in that aminomethyl is particularly advantageous with respect to the incorporation of "spacer" or "handle" groups owing to the reactivity of the amino group of the aminomethyl functionality with respect to the essentially quantitative formation of amide bonds to a carboxylic acid group at one end of the spacer-forming reagent. A vast number of relevant spacer- or handle-forming bifunctional reagents have been described (see Barany et al., *Int. J. Peptide Protein Res.*, 30, 705–739 (1987), especially reagents which are reactive towards amino groups, such as the amino group in the aminomethyl function, including a 4-(haloalkyl)aryl-lower alkanoic acid such as 4-(bromomethyl)phenylacetic acid, a Boc-aminoacyl4-(oxymethyl)aryl-lower alkanoic acid such as Boc-aminoacyl4-(oxymethyl)phenylacetic acid, N-Boc-p-acylbenzhydrylamine such as N-Boc-p-glutaroylbenzhydrylamine, N-Boc-4'-lower alkyl-p-acylbenzhydrylamine such as N-Boc-4'-methyl-p-glutaroylbenzhydrylamine, N-Boc-4'-lower alkoxy-p-acylbenzhydrylamine such as N-Boc-4'-methoxy-p-glutaroylbenzhydrylamine and 4-hydroxymethylphenoxy-lower alkanoic acid such as 4-hydroxymethylphenoxyacetic acid.

Certain functionalities, such as benzhydrylamine, 4-methylbenzhydrylamine and 4-methoxybenzhydrylamine which may be incorporated for the purpose of cleavage of a synthesized peptide or protein chain from the solid support such that the C-terminal of the peptide or protein chain is in amide form, require no introduction of a spacer group, and any such functionality may advantageously be employed in the context of the present invention.

An alternative strategy concerning the introduction of spacer or handle groups is the so-called "pre-formed handle" strategy (see Tam et al., *Synthesis*, 955–57, (1979)), which offers complete control over coupling of the first amino acid, and excludes the possibility of complications arising from the presence of undesired functional groups not related to the peptide or protein synthesis.

In this strategy, spacer or handle groups, in general spacer or handle groups of the same types as described above, are reacted with the first amino acid which it is desired to anchor to the solid support, the amino acid being N-protected and optionally protected at other side chains which are not relevant with respect to the building-up of the desired peptide or protein chain. Suitable N-protecting groups are Boc, normally in combination with benzyl groups for the protection of side chains, and Fmoc, normally in combination with t-butyl for the protection of any side chains (Boc=t-butyloxycarbonyl; Fmoc=9-fluorenylmethyloxycarbonyl), although a number of other possibilities exist which are well known in conventional solid-phase peptide synthesis.

Thus, in those cases in which a spacer or handle group is desirable, the first amino acid to be coupled to the solid support can either be coupled to the free reactive end of a spacer group which has been bound to the initially introduced functionality, for example aminomethyl, or can be reacted with the spacer-forming reagent, which in turn is then reacted with the initially introduced functionality.

Following completion of the coupling of the first amino acid which is to be coupled, the next stage of the solid-phase synthesis is the systematic elaboration of the desired peptide or protein chain. This elaboration involves repeated deprotection/coupling cycles. The temporary protecting group, such as a Boc or Fmoc group as described above, on the last-coupled amino acid is quantitatively removed by a suitable treatment, for example by acidolysis, such as with trifluoroacetic acid, in the case of Boc, or by base treatment, such as with piperidine, in the case of Fmoc, so as to liberate the N-terminal amine function of the last-coupled amino acid.

The next desired N-protected amino acid is then coupled to the N-terminal of the last-coupled amino acid. This coupling of the C-terminal of an amino acid with the N-terminal of the last-coupled amino acid can be achieved in several ways, for example by providing the incoming amino acid in a form with the carboxyl group activated by any one of several methods, including the initial formation of an active ester derivative, or the initial formation of an anhydride. Alternatively, the carboxyl group of the incoming amino acid may be reacted directly with the N-terminal of the last-coupled amino acid with the assistance of a condensation reagent, for example dicyclohexylcarbodiimide or derivatives thereof.

Following the completed assembly of the desired peptide or protein chain, including protecting groups, the next step will normally be deprotection of the amino acid moieties of the peptide or protein chain and cleavage of the synthesized peptide or protein from the solid support. These processes can take place substantially simultaneously, thereby providing the free peptide in the desired form. Alternatively, in cases in which condensation of two separately synthesized peptide or protein chains is to be carried out, it is possible by choosing a suitable spacer group at the start of the synthesis to cleave the desired peptide or protein chains from their respective solid supports, both peptide or protein chains still incorporating their side-chain protecting groups, and finally removing the side-chain protecting groups after, for example, coupling the two side-chain protected peptide or protein chains to form a longer peptide or protein chain. A third possibility, which is particularly relevant for example in the case of analytical aspects of peptide chemistry or biochemist, is to remove the side-chain protecting groups from the synthesized peptide or protein chain without cleaving the anchoring linkage holding the chain to the solid support. This aspect is discussed further, below.

It is envisaged that polystyrene-grafted cross-linked polyolefin substrates analogous to those of the present invention, but comprising linker or spacer groups adapted to the particular chemistry in question, may be valuable in the synthesis of single or multiple biopolymer molecules other than peptides. One example would be the synthesis of oligonucleotides, these being conceptually simple to synthesize since only four different reaction compartments are normally required, one for each of the four nucleotide units involved (i.e. A, T, G and C for DNA fragments, or A, G,. C and U for RNA fragments). Such syntheses could be carried out in a parallel and substantially simultaneous fashion, in a manner analogous to that described within the context of the present invention.

For a number of uses, e.g. in a number of solid phase bioassays, the functionality is advantageously a functionality such that the anchoring linkage ensures substantially permanent anchoring linkage of the species attached to the substrate. Such a permanent attachment may, e.g., be a covalent binding. By the term "substantially permanent anchoring linkage" is meant a bond which under the conditions prevailing in the course of the various reactions and treatments to which the amino acid-, peptide- or protein-bearing substrate is exposed (e.g. further coupling of protected and/or derivatized amino acids or peptides, removal of protecting groups, washing, exposure to body fluids, etc.) during the various steps involved in applying it to a bioassay procedure is stable with respect to release or loss of the attached (coupled) species.

Such a substantially permanent linkage may, e.g., be a linkage derived from an amino-substituted alkyl group, preferably aminomethyl.

A substantially permanent anchoring linkage may be obtained by omitting a spacer group, or by using a spacer group which will ensure a substantially permanent anchoring linkage. Such as spacer group may be one derived from the group consisting of straight and branched chain omega-aminoalkanoic acids, preferably a spacer group derived from the group consisting of 6-aminohexanoic acid, 5-aminopentanoic acid, 4-aminobutanoic acid and 3-aminopropanoic acid.

In the following, some examples of solid phase bioassay uses of the polymer-grafted polyolefin substrates according to the invention are discussed.

As indicated above, the polymer-grafted polyolefin substrates according to the invention can suitably be used as supports for components in immune assays such as ELISAs or RLAs. In such embodiments the substrates could be used as, or as coatings on, a wide variety of surfaces, such as titer plate wells, beads, hollow fibers, filter surfaces etc.

One possibility is to synthesize the antigenic peptides onto the substrates according to the invention in situ (substantially as mentioned above and as described in Example 6). In this way a coated surface suitable for multiple use could be prepared. The modus operandi for using such a surface in an assay would be to contact the surface with specific binding ligands (e.g. in the form of a polyvalent antiserum directed against the peptide). If ligands bind to the surface they can be detected by adding labelled anti-ligands as in a traditional immune assays (of course, several enhancement steps comprising anti-antibodies could be introduced in order to increase sensitivity by obtaining a tree-like structure, wherein the "root" is the coupled antigen). The difference from traditional immune assays would be that the step of non-specific binding of the peptide to e.g. a well in a titer-plate could be omitted, as the plate already has the peptide firmly bound to the surface. Thus, diagnostic kits containing fewer reactants than those normally encountered commercially are interesting embodiments of the present invention. On the other hand, a very important embodiment is where the substrate is provided with a functionalization such that a peptide or protein, or DNA, can be coupled to the functionalized grafted polymer, e.g. by a condensation reaction, e.g. using a carbodiimide.

Suitable peptides to be permanently linked to such a surface could be pre-identified epitopes of polypeptides which are subject to routine screens in the medical or veterinarian field (antigens from microorganisms such as pathogenic bacteria, virus, protozoans, fungi, helminths).

It goes without saying that also antibodies directed to one epitope of an antigen can be coupled to the substrates of the invention. In such a way a "sandwich assay" can be prepared, wherein 1) a sample containing the antigen is added, and 2) a (optionally labelled) antibody directed against another epitope of the same antigen is added after removal of unbound antigen.

Thus, following these strategies, it is possible to determine the presence of antigens as well as antibodies directed against these antigens in samples from various sources.

Another possibility is to use DNA fragments which are coupled permanently, e.g. covalently, to the substrates of the invention (e.g. carbodiimide coupled to aminomethylated substrates of the invention). Such DNA fragments can be used in a manner analogous to the use of antigens/antibodies, as the fragments can be chosen so as to hybridize with high specificity to other nucleic acid fragments; the latter should have a free end to which a new labelled) hybridization partner is added.

Assays using this strategy are especially suited for the determination of infections with microorganisms, as the detection of nucleic acid fragments from such infectants is proof of ongoing infection. Dependent on the stringency conditions of the hybridization assay as well as the specificity of the coupled DNA fragment, it is possible to either determine the species of e.g. an infectious agent (microorganism) or even, if desired, the specific strain.

Instead of a hybridization assay as such, the substrate coupled DNA can bind nucleic acids to be later used in a PCR amplification. This use of the substrates of the invention could then serve as a "fishing-hook" for complementary DNA fragments and the coupled DNA could optionally serve as the one of two primers used in the PCR amplification (if an amble amount of coupled primer is present).

It is of course also possible to use DNA analogues instead of DNA as the substance coupled to the substrate according to the invention. This choice may give a higher degree of freedom in the hybridization step.

All of the above-sketched embodiments can also be used in other scenarios where it is desired to have the one of two binding partners affixed to a surface, e.g. on chromatographic beads in a column (for affinity chromatography) and the like.

Depending of the choice of the grafted polymer it is possible to couple substances to the substrates of the invention in a non-covalent manner.

One way of achieving this is to couple, to the substrates of the invention, substances capable of coordinating metal ions on the surface; an example of such an embodiment is NTA coupled to agarose, where NTA is a substituted nitrilotriacetic acid. Such a surface is capable of being charged with $Ni^{2+}$ ions which can bind polyhistidinyl residues in a polypeptide with high affinity.

The following examples illustrate the invention, the abbreviations used being as follows:

LIST OF ABBREVIATIONS

AM: 2-(N,N-dimethylcarbamyl)ethyl
BHA: 4-benzhydrylamine
BHT: 2,6-di(tert-butyl)-p-cresol
Boc: tert-butyloxycarbonyl
BrZ: 2-bromobenzyloxycarbonyl
Bzl: benzyl
ClZ: 2-chlorobenzyloxycarbonyl
DCC: N,N'-dicyclohexylcarbodiimide
DCM: dichloromethane
DCU: N,N'-dicyclohexylurea
DIC: N,N'-diisopropylcarbodiimide
DIEA: N,N-diisopropylethylamine
DMF: N,N-dimethylformamide
FABMS: Fast atom bombardment mass spectrometry
HOBt: 1-hydroxybenzotriazole
HPLC: high performance liquid chromatography
Pam: phenylacetamidomethyl
PE: polyethylene
PEO: 3,6,9-trioxadecanoyl
PP: polypropylene
PS: polystyrene
SEC: size-exclusion chromatography
SPPS: solid phase peptide synthesis
TFA: trifluoroacetic acid
TFMSA: trifluoromethanesulfonic acid
THF: tetrahydrofuran
Tos: tosyl (i.e. p-toluenesulfonyl)
XLPE: cross-linked polyethylene The abbreviations used for the various amino acids are in accordance with the recommendations of the IUPAC-IUB Commission of Biochemical Nomenclature [J. Biol. Chem., 247, 977–983 (1972)], and refer in all cases to L-configuration amino acids.

Unless otherwise indicated, reagents and solvents etc. employed in the following examples are commercially available.

The Boc-protected 3-(4-benzhydrylamine)propionic acid used in Example 3(b) below was prepared as follows:

Hydrocinnamic acid chloride was prepared from commercially available hydrocinnamic acid (Aldrich) using thionyl chloride. The acid chloride was converted to the corresponding amide by reaction with 25% aqueous ammonia at a temperature below 0° C., and Friedel-Crafts acylation of the isolated amide using benzoyl chloride and aluminium chloride in $CS_2$ afforded the corresponding benzophenone in excellent yield (95%). The latter was transformed to 3-(4-benzhydrylamine)-propionic acid by reduction of its oxime using zinc in acetic acid followed by hydrolysis of the amide functionality. The Boc-protected acid was prepared as described by Stewart and Young, *Solid Phase Peptide Synthesis*, 2nd Ed., Pierce Chemical Company, 1984, pp. 63 and 61, and was recrystallized twice from n-hexane/toluene.

EXAMPLE 1

Preparation of Cross-linked Polyethylene Sheet or Film

Clear, low-density polyethylene film of thickness 54 μm (a PE film of the same type as employed in Example 1 of WO 90/02749 for the preparation of polystyrene-grafted polyethylene film) were irradiated to different absorbed doses with high-energy electrons from an electron accelerator installed at Forskningscenter Risø (Risø National Laboratory); the latter accelerator produces electrons of energy 10 MeV, which ensures complete penetration into material of thickness up to about 3.5 cm (for material of density 1 $g/cm^3$), but it should be made clear here that electrons of considerably lower energy, e.g. of the order of a few hundred keV, will be quite adequate to ensure complete penetration of a film of the thickness employed in the present example.

The absorbed doses (in kGy) for various samples of film irradiated in this manner are given in Table 1 in Example 2, below.

Apart from a faint yellowish colouration (characteristic of irradiated polyethylene), the irradiated film samples (XLPE film) are visually and dimensionally indistinguishable from the unirradiated PE film.

EXAMPLE 2

Preparation of Polystyrene-grafted Cross-linked Polyethylene Film

Sheets of XLPE film prepared as described in Example 1 (vide supra) were immersed in a 30% (v/v) solution of styrene in methanol (both of the latter being of at least good reagent grade) in an aluminium container equipped with a lid. The container and contents were then irradiated in a $^{60}$Co gamma-irradiation facility. The dose rate was approximately 1.2 kGy/hour, and the total absorbed dose was 5.8 kGy.

After irradiation, the film was removed from the container, rinsed/washed with toluene and allowed to dry in the air.

A surprising and very advantageous feature of PS-grafted XLPE film prepared in the above manner is that the film contains no detectable quantity of occluded polystyrene homopolymer, and the grafted film therefore requires no special treatment after grafting to remove such homopolymer. This is in marked contrast to the PS-grafted PE film prepared according to WO 90/02749, which requires prolonged extraction (at least about 30 hours) in a Soxhlet apparatus with a solvent such as dichloromethane in order to ensure satisfactory removal of occluded homopolymer.

Figure 3A:
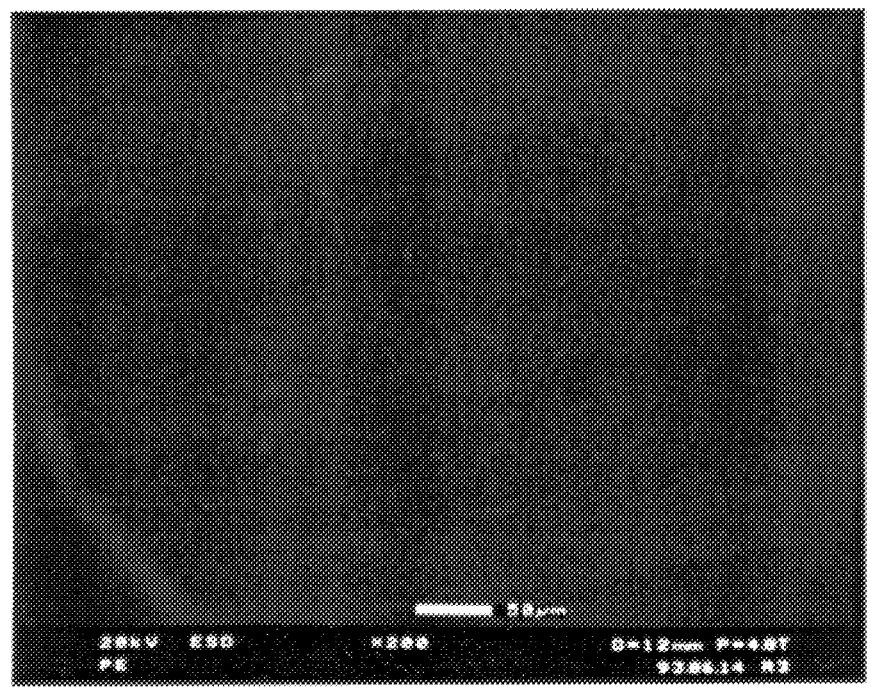
FIG. 3. Scanning electron micrographs of: (A) ungrafted PE film; and (B) 188% PS-grafted PE film in accordance with WO 90/02749 (magnification 200×). The scale bar in the photographs represents 50 μm in both cases.
Figure 3B:
Figure 4A:
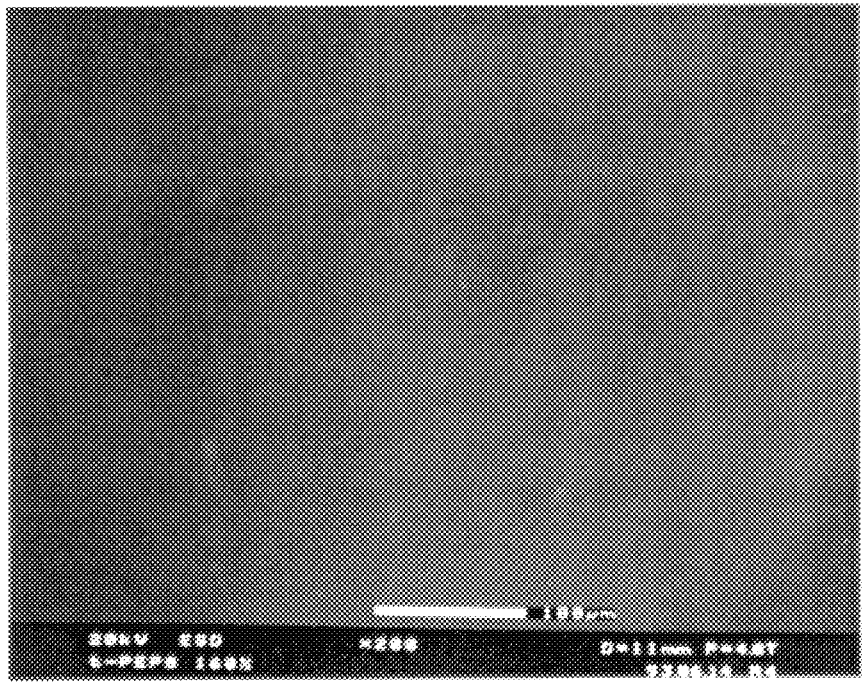
FIG. 4. Scanning electron micrographs of (A) 168% PS-grafted XLPE film and (B) 200% PS-grafted XLPE film (magnification 200×). The distance represented by the scale bar is given on the photographs. It is apparent that the homogeneity of the films in question is similar to that of the film shown in FIG. 3(A) (ungrafted, non-cross-linked PE film), and the films show no sign of the presence of bubbles or blisters (due to occluded homopolymer) such as are clearly visible in FIG. 3(B).
Figure 4B:
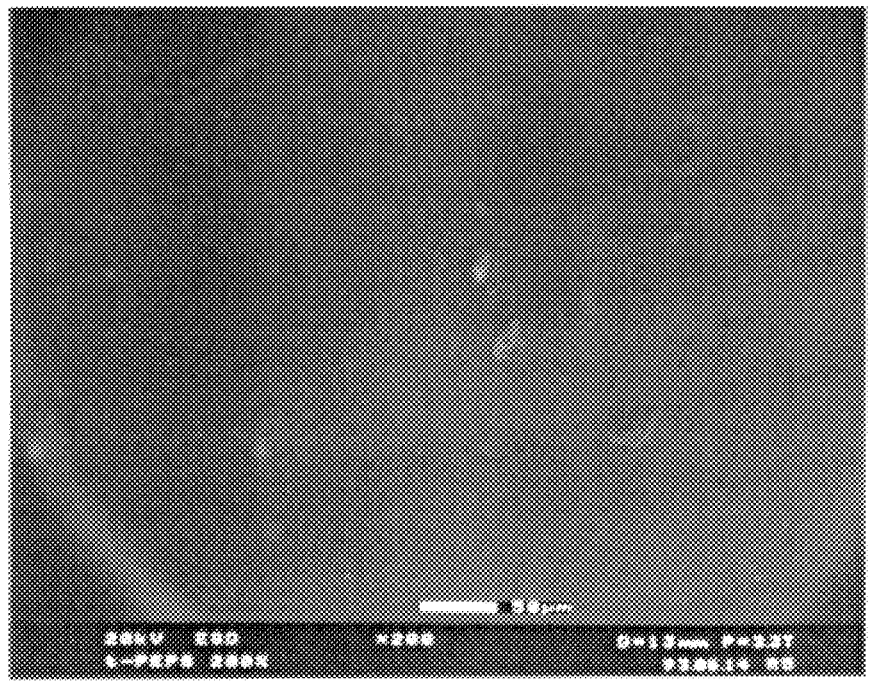
Figure 5:
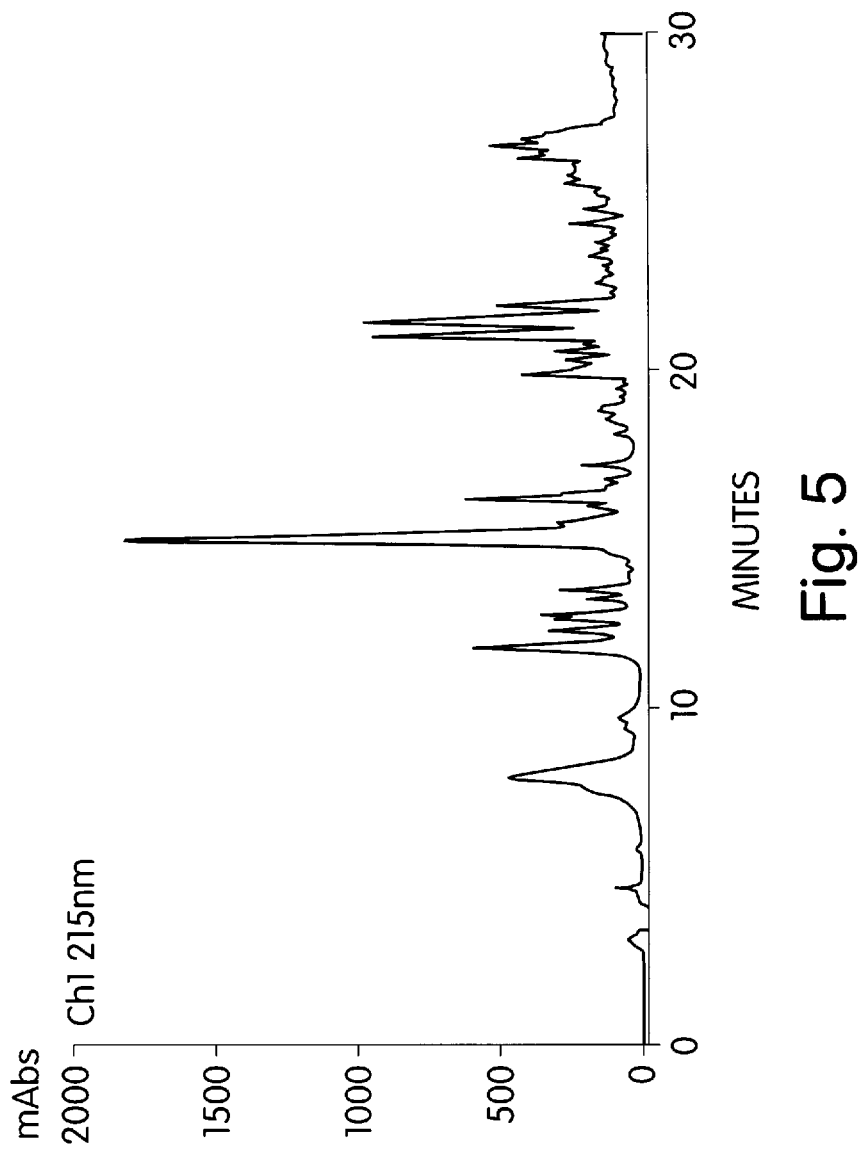
FIG. 5. Analytical HPLC chromatogram of H-Tyr-Asp-Ala-Lys-Ser-Gly-Phe-Lys-Thr-Ala NH$_2$, synthesized on an MBHA derivatized polystyrene-grafted cross-linked polyethylene tube as described in Example 10. A Nucleosil C$_{18}$ reverse-phase column (5 μm, 0.46×25 cm) was employed.

With respect to homogeneity, the PS-grafted XLPE film shows no signs of the presence of the small bubbles or blisters which have been found to be present in PS-grafted PE film prepared according to WO 90/02749, and which are believed to be attributable to the occlusion of polystyrene homopolymer within the PS-grafted PE film during the grafting process (see FIGS. 3 and 4). As a result, the light transmission and reflection properties of PS-grafted XLPE film are far better than those of PS-grafted PE film, and resemble those of ungrafted PE film.

The grafting results for the various samples of XLPE film are shown below in Table 1, together with the result obtained using a sample of PE film which had not been subjected to cross-linking treatment (i.e. a sample of PE film identical to that used as starting material in Example 1, above).

As can be seen from the table, the percentage of grafting on the XLPE film samples varies very little from sample to sample (ranging from 230 to 260%) and is only moderately lower than for the PE film. Since the irradiation conditions for the XLPE and PE film were identical, it thus appears that the polystyrene chains grafted to the two types of film are of comparable length.

TABLE 1

Grafting of XLPE sheets in methanol/styrene (70/30 v/v)

| Radiation dose used for cross-linking of PE film$ (kGy) | % Polystyrene grafted to the XLPE film* |
|---|---|
| 0 | 336 |
| 51 | 260 |
| 97 | 250 |
| 148 | 234 |
| 195 | 230 |
| 248 | 249 |
| 296 | 249 |

$Dose for incipient gel formation in this type of PE is 50 kGy. (The polyolefin material is per definition cross-linked when the dose is the dose for incipient gel formation or higher)
*Graft % = [(mass of final film) − (mass of XLPE)] × 100/(mass of XLPE). Grafting performed using $^{60}$Co gamma irradiation, dose 5.8 kGy.

EXAMPLE 3

Functionalization/activation of PS-grafted XLPE Film (a) Preparation of Aminomethylated Film 14 g of a 168% PS-grafted XLPE film [prepared as described in Example 2 from XLPE film (electron irradiation dose 296 kGy) but using a lower γ radiation dose] was cut into eight essentially identical rectangular pieces which were then placed in a 300 ml SPPS reaction vessel on a manual SPPS shaker and washed with 200 ml of TFA/CH$_2$Cl$_2$ (1:1 v/v) for 10 min. A solution of 1.0 g (5.46 mmol) N-(hydroxymethyl)phthalimide (97% purity; EGA-CHEMIE) in 200 ml of TFA/CH$_2$Cl$_2$ (1:1 v/v) was added to the washed pieces of film, and the "mixture" was shaken for 10 min. 50 ml of TFMSA/TFA/CH$_2$Cl$_2$ (11:18.5:18.5 v/v/v) was added slowly (ca. 2.5 ml portions) over a 6 hour period and shaking was continued for another 18 hours. The pieces of film were isolated by filtration and washed sequentially with the following: CH$_2$Cl$_2$ (200 ml, 4× 15 min), methanol (200 ml, 1×15 min), and ethanol (200 ml, 1×15 min). They were then shaken in a solution of 200 ml of ethanol and 30 ml of hydrazine hydrate for 22 hours at 60° C., the heating being achieved by means of a flexible electric heating belt wrapped around the reaction vessel. The sheets were filtered from the hot mixture and washed sequentially with the following: hot ethanol (200 ml, 60° C., 3×20 min), hot DMF (200 ml, 60° C., 2×20 min), hot methanol (200 ml, 50° C., 2×10 min), methanol (200 ml, 1×10 min), and CH$_2$Cl$_2$ (200 ml, 3×15 min). Finally, the sheets were treated (neutralized) with 200 ml of DIEA/CH$_2$Cl$_2$ (1:9 v/v) for 2×10 min, washed with CH$_2$Cl$_2$ (200 ml, 4×10 min), and dried at room temperature. A total of six quantitative Kaiser ninhydrin tests [Sarin et al., Anal. Biochem., 117, 147 (1981)] indicated a degree of substitution (aminomethylation) of 0.37±0.09 mmol of NH$_2$ groups per gram of film.

Aminomethylation of a 200% PS-grafted XLPE film (prepared as in Example 2 but using a slightly higher γ radiation dose than for the 168% PS-grafted XLPE film) was carried out analogously to give a film with a degree of substitution of 0.84±0.13 mmol NH$_2$ per g.

(b) Preparation of Boc-protected 4-benzhydrylamine-derivatized Film

Boc-protected 3-(4-benzhydrylamine)propionic acid was coupled as the HOBt ester to the 0.37 mmol NH$_2$/g aminomethylated PS-grafted XLPE film prepared as in Example 3(a), above, using the following procedure:

2.7 g of the aminomethylated film was pre-washed in 70 ml of DMF/CH$_2$Cl$_2$ (1:2 v/v) for 3×3 min in a 100 ml reaction vessel on a manual SPPS shaker. 2.49 g (7 mmol) of Boc-protected 3-(4-benzhydrylamine)propionic acid and 1.07 g (7 mmol) of HOBt were dissolved in 50 ml of DMF/CH$_2$Cl$_2$ (1:1 v/v), and the solution was stirred in a screw-capped tube for 3 min at 0° C. A solution of 1.1 ml of DIC in 20 ml of CH$_2$Cl$_2$ was added, and the mixture was then stirred for 25 min at 0° C. and added to the pre-washed aminomethylated film. After shaking the resulting "mixture" for 3 hours, the film was isolated by filtration, washed with CH$_2$Cl$_2$, neutralized with DIEA/CH$_2$Cl$_2$ (5:95 v/v), washed with CH$_2$Cl$_2$ and dried in vacuo. Quantitative Kaiser ninhydrin tests (vide supra) indicated that ca. 0.08 mmol of the initial 0.37 mmol of amino groups per gram of film had not coupled to the Boc-protected BHA reagent. These remaining free amino groups were acetylated ("capped") using acetic anhydride/pyridine/CH$_2$Cl$_2$ (1:1:2 v/v/v), leaving only 0.006 mmol of uncapped, free amino groups per gram (as determined by quantitative Kaiser ninhydrin testing).

A piece of the film was deprotected by treatment with TFA/CH$_2$Cl$_2$ (1:1 v/v) for 2×1 min and 1×30 min, and subsequent quantitative Kaiser ninhydrin testing of the deprotected film indicated Boc-protected BHA derivatization of ca. 0.27 mmol of amino groups per gram of film, which agrees well with the expected value of ca. 0.28 mmol/g (it should be noted that because of the gain in weight of the film when ca. 0.3 mmol of BHA derivative per gram is coupled to the aminomethylated film, the calculated theoretical degree of substitution, i.e. mmol BHA/g of derivatized film, decreases to ca. 93% of the initial value for mmol $NH_2$/g of aminomethylated film.

For unknown reasons, attempts to derivatize the aminomethylated film directly using Boc-protected 3-(4-benzhydrylamine)propionic acid (instead of the HOBt ester thereof) and 0.1M DIC in $CH_2Cl_2$ resulted in only ca. 50% substitution/derivatization.

(c) Preparation of Boc-Tyr(BrZ)-Pam-film

Boc-Tyr(BrZ)-4-(oxymethyl)phenylacetic acid [prepared by the procedure of Tam et al., *Synthesis* (1979) 955–57] was coupled as the HOBt ester to the 0.84 mmol $NH_2$/g aminomethylated PS-grafted XLPE film prepared as in Example 3(a), above, using the following procedure:

0.62 g of the aminomethylated film was pre-washed in 20 ml of DMF/$CH_2Cl_2$ (1:2 v/v) for 3×3 min in a 25 ml reaction vessel on a manual SPPS shaker. 1.86 g (2.8 mmol) of Boc-Tyr(BrZ)4-(oxymethyl)phenylacetic acid, 429 mg (2.8 mmol) of HOBt and 576 mg (2.8 mmol) of DCC were dissolved in 21 ml of DMF/$CH_2Cl_2$ (1:1 v/v), and the solution was stirred for 1 hour, filtered and added to the prewashed aminomethylated film. After shaking the resulting "mixture" overnight, the film was isolated by filtration, washed with $CH_2Cl_2$, neutralized with DIEA/$CH_2Cl_2$ (5:95 v/v), washed with $CH_2Cl_2$ and dried in vacuo. Quantitative Kaiser ninhydrin tests (vide supra) indicated that ca. 0.008 mmol of the initial 0.84 mmol of amino groups per gram of film had not coupled to the Boc-protected reagent. These remaining free amino groups were acetylated as in Example 3(b), above, leaving only 0.004 mmol of uncapped, free amino groups per gram (as determined by quantitative Kaiser ninhydrin testing).

A piece of the film was deprotected as in Example 3(b), and subsequent quantitative Kaiser ninhydrin testing of the deprotected film indicated Boc-Tyr(BrZ)-Pam- substitution of ca. 0.57 mmol of amino groups per gram of film, which agrees well with the expected value.

As in Example 3(b), and for unknown reasons, attempts to derivatize the aminomethylated film directly using Boc-Tyr (BrZ)-4-(oxymethyl)-phenylacetic acid (instead of the HOBt ester thereof) and DCC resulted in only ca. 20% substitution.

EXAMPLE 4

Preparation of Hydrophilic Films (a) Preparation of High-level Aminomethylated PS-grafted XLPE Film A piece (2.8317 g, ca. 17.1 mmol) of 168% PS-grafted XLPE film as employed in Example 3(a), above, was washed twice with $CH_2Cl_2$ and then shaken for 10 min in a solution of 3.1769 g (17.9 mmol) of N-(hydroxymethyl) phthalimide in 200 ml of TFA/$CH_2Cl_2$ (1:3 v/v). Two 1.0 ml portions of TFMSA were then added with an interval of one hour, and the "mixture" was then shaken slowly overnight. The light yellow film was washed three times with $CH_2Cl_2$ and twice with chloroform. Elementary analysis at this stage indicated the nitrogen content of the film to be 4.11%, corresponding to 91.5% substitution of the aromatic rings of the polystyrene part of the film. This intermediate film swells in $CH_2Cl_2$, DMF and chloroform. When dry, or in solvents with little or no swelling ability, the film becomes rigid and fragile. For this reason the intermediate film is suitably stored in $CH_2Cl_2$ if there is to be a delay before completing the aminomethylation procedure.

To a sample of this intermediate film (corresponding to 1.383 g of the 168% PS-grafted XLPE film used as starting material) was added 200 ml of a 10% v/v solution of hydrazine hydrate in ethanol, and the "mixture" was allowed to stand without shaking at 50° C. for six hours and then shaken overnight The swelled sample were washed twice with hot ethanol, thrice with chloroform, thrice with $CH_2Cl_2$ and six times with DMF/$CH_2Cl_2$.

The product, i.e. high-level aminomethylated film, may be stored in $CH_2Cl_2$; however, on prolonged storage for more than about 3 weeks at room temperature it becomes rigid.

(b) Preparation of Boc-protected 4-benzhydrylamine-derivatized High-level Aminomethylated Film This was performed using a procedure analogous to that described in Example 3(b) (vide supra), but starting from the product sample prepared according to Example 4(a), together with 1.0 mmol of Boc-protected 3-(4-benzhydrylamine)propionic acid and the corresponding amount of DIC. The resulting film was subjected to a "standard washing procedure" (referred to as such elsewhere herein) involving shaking the film twice in DMF, twice in $CH_2Cl_2$, twice in DIEA/$CH_2Cl_2$ (5:95 v/v) and then four times in $CH_2Cl_2$.

(c) Preparation of 2-(N,N-dimethylcarbamyl)ethyl-modified, Boc-protected 4-benzhydrylamine-derivatized Film A portion of product film prepared according to Example 4(b) above (equivalent to 0.898 g of 168% PS-grafted XLPE film) was shaken overnight at 50°–55° C. with 200 ml of a 10% w/v solution of N,N-dimethylacrylamide in DMF containing 1 mg of BHT. The film was then subjected to the standard washing procedure described in Example 4(b), above.

Quantitative Kaiser ninhydrin testing indicated that 0.076 mmol of $NH_2$ groups per gram of film remained unsubstituted. The film was acetylated as described in Example 3(b), subjected to the standard washing procedure, subjected to further acetylation for 2 hours using 0.5M acetylimidazole in $CH_2Cl_2$, and finally washed by the standard washing procedure. Quantitative Kaiser ninhydrin testing indicated that only 0.0061 mmol of $NH_2$ groups per gram of film then remained unsubstituted.

The resulting film (which for convenience is denoted Boc-BHA/AM-film) is highly transparent and uniform in appearance. It swells in solvents such as, e.g., $CH_2Cl_2$, DMF, ethanol and—particularly interestingly—in water. When dried (i.e. free of solvents capable of swelling the film) the film is fragile, whereas the swollen film is soft and pliable. The swollen hydrophilic film is somewhat less resistant to tearing than the non-hydrophilic film.

The content of BHA groups in Boc-BHA/AM-film prepared in the above manner was determined by quantitative Kaiser ninhydrin tests after deprotecting the BHA groups using TFA/$CH_2Cl_2$ (1:1 v/v). The results indicated 0.116±0.014 mmol of BHA amino groups per gram of film.

(d) Preparation of 3,6,9-trioxadecanoyl-modified, Boc-protected 4-benzhydrylamine-derivatized Film A portion of product film prepared according to Example 4(b) above (equivalent to 0.485 g of 168% PS-grafted XLPE film) was subjected to the standard washing procedure. It was then shaken for 16 hours in a solution of 3,6,9-trioxadecanoic acid [prepared according to U. Heilmann and F. Vögtle, *Liebigs Ann. Chem.* (1980) 858–862], HOBt and DIC (concentration of all three reagents 0.1M) in $CH_2Cl_2$/DMF (1.1 v/v). The film was subjected to the standard washing procedure, shaken again for 16 hours in 3,6,9-trioxadecanoic acid/HOBt/DIC solution as before, and finally washed using the standard washing procedure.

Quantitative Kaiser ninhydrin testing indicated that only 0.0017 mmol of $NH_2$ groups per gram of film remained unsubstituted, and the film was therefore not subjected to any further treatment to reduce the number of unsubstituted amino groups.

As with the film prepared according to Example 4(b), the resulting film (which for convenience is denoted Boc-BHA/PEO-film) is highly transparent and uniform in appearance, and it swells in solvents such as $CH_2Cl_2$, DMF, ethanol and water. The film is soft and pliable when swollen, and is considerably more resistant to tearing than the AM-modified film prepared according to Example 4(c).

The content of BHA groups in Boc-BHA/PEO-film prepared in the above manner was determined by quantitative Kaiser ninhydrin tests after deprotecting the BHA groups using $TFA/CH_2Cl_2$ (1:1 v/v). The results indicated 0.105±0.008 mmol of BHA amino groups per gram of film.

EXAMPLE 5

Hygroscopicity of the Hydrophilic Films (Boc-BHA/AM-film and Boc-BHA/PEO-film)

Samples of the two types of film were dried overnight over $P_2O_5$ at a pressure of approximately 0.005 mmHg until constant weight was attained. Upon exposing the thus-dried films to air at 25° C. and 50% relative humidity the gain in weight was as follows:

Boc-BHA/AM-film: 16.7%

Boc-BHA/PEO-film: 20.4%

Before weighing prior to, e.g., quantitative Kaiser ninhydrin tests, the films were washed with $CH_2Cl_2$ and dried at approximately 0.005 mmHg for at least one hour, the weight of the films becoming constant after ca. 30 minutes.

EXAMPLE 6

Peptide Synthesis

General procedures: Standard solid-phase reaction vessels [Merrifield et al. *Biochemistry* 21 (1982) 5020] were employed for the syntheses. The quantitative Kaiser ninhydrin test (vide supra) was used routinely throughout the syntheses to determine the extent of amino acid coupling as well as deprotection. However, all ninhydrin values in the following are only indicative values, since they are not corrected for potential background, and since it is not known how well the normally employed extinction coefficients can be applied.

HF reactions were carried out in a Diaflon HF apparatus from Toho Kasei (Osaka, Japan). A μBONDAPAK™ $C_{18}$ (Waters) reverse-phase column (5 μm, 0.46×30 cm) was used for analytical HPLC of the peptides on a SP 8000 instrument. Buffer A for the elution gradient was 5% v/v acetonitrile in water containing 445 μl of TFA per liter, and buffer B was 60% v/v acetonitrile in water containing 390 μl of TFA per liter. The flow rate was 1.5 ml/min, and the linear elution gradient employed was 0–100% of buffer B over a period of 30 min. The eluents from the column were monitored spectrophotometrically at 215 nm.

The crude peptides were purified on a semi-preparative $C_{18}$ reverse-phase column (5 μm, 1.0×25 cm), and the molecular weight of the purified products was determined by FABMS.

Synthetic protocol: Unless otherwise stated, the syntheses were carried out employing the following double coupling protocol for coupling of Boc-Phe, Boc-Val, Boc-Leu, Boc-Gly, Boc-Ser(Bzl), Boc-Thr(Bzl) and Boc-Lys(ClZ):

(1) Boc-deprotection with $TFA/CH_2Cl_2$ (1:1 v/v; 2×1 min and 1×30 min);

(2) Washing with $CH_2Cl_2$ (6×1 min);

(3) Neutralization with $DIEA/CH_2Cl_2$ (1:19 v/v; 2×2 min and 2×1 min);

(4) Washing with $CH_2Cl_2$ (4×1 min);

(5) Samples of the film support were occasionally cut off to check the deprotection, and thereby the number of growing peptide chains, by means of the quantitative Kaiser ninhydrin test;

(6) In situ coupling with 0.1M Boc-amino acid and 0.1M DIC dissolved in $CH_2Cl_2$. The coupling reaction was allowed to proceed for a total of 2 hours (with shaking);

(7) Washing with DMF (2×2 min) and $CH_2Cl_2$ (2×2 min);

(8) Neutralization with $DIEA/CH_2Cl_2$ (1:19 v/v; 2×2 min);

(9) Washing with $CH_2Cl_2$ (4×1 min);

(10) Samples of the film support were occasionally cut off (and neutralized) to check completeness of the coupling reaction by means of the quantitative Kaiser ninhydrin test;

(11) A second coupling was performed with the amino acid in the form of 0.1M pre-formed symmetrical anhydride in 50% $DMF/CH_2Cl_2$ with shaking for 2 hours;

(12) Repetition of steps (7)–(10);

(13) In selected positions (where appropriate) acetylation ("capping") was performed using acetic anhydride/pyridine/$CH_2Cl_2$ (1:1:2 v/v/v);

(14) When a capping step had been performed, a quantitative Kaiser ninhydrin test was occasionally carried out to check the extent of substitution.

Synthesis of H-Gln-Arg-Leu-Phe-Gln-Val-Lys-Gly-Arg-Arg-$NH_2$ on Film Supports and on Standard Polystyrene Beads Human gelsolin fragment 160–169, i.e. H-Gln-Arg-Leu-Phe-Gln-Val-Lys-Gly-Arg-Arg-$NH_2$ [designated hGS-(160–169)], was synthesized on the BHA derivatized forms of (a) the PS-grafted XLPE film, (b) the hydrophilic PEO-modified PS-grafted XLPE film, and (c) on the hydrophilic AM-modified PS-grafted XLPE film, as well as on (d) a commercially available, BHA-derivatized standard polystyrene resin in bead form, i.e. a resin of the "Merrifield" type (Peninsula Laboratories, San Francisco, USA).

The synthesis employed conventional solid-phase chemistry, using the TFA-labile Boc group for temporary protection, and the HF-labile 2-chlorobenzyloxycarbonyl (ClZ) and tosyl (Tos) groups for "permanent" protection of Lys and Arg, respectively. The structure of the fully protected hGS-(160–169) is Boc-Gln-Arg(Tos)-Leu-Phe-Gln-Val-Lys(ClZ)-Gly-Arg(Tos)-Arg(tos)-BHA-support. The solid-phase assembly followed the synthetic protocol outlined above, with the following modifications:

1) Boc-Gln was double coupled as HOBt ester to minimize the dehydration of amide to nitrile [Mojsov et al., *J. Org. Chem.* 45 (1980) 555]; the HOBt ester was formed in situ by combining equimolar (0.1M concentration) amounts of Boc-Gln, DCC and HOBt in $DMF/CH_2Cl_2$ (3:7 v/v) in the reaction vessel.

2) For coupling of Boc-Phe$^{163}$ to Gln$^{164}$, both the first and the second coupling were with the pre-formed symmetrical anhydride in DMF/CH$_2$Cl$_2$ (2:8 v/v) to minimize pyrrolidone carboxylic acid formation [DiMarchi et al., *Int. J. Peptide Protein Res.* 19 (1982) 88].

The fully protected hGS-(160–169) was treated with TFA/CH$_2$Cl$_2$ (1:1 v/v) to remove the N-terminal Boc group prior to HF cleavage. Deprotection and release of the free hGS-(160–169) from the film supports was accomplished (individually) using a 10% solution of anisole in anhydrous HF, with stirring at 0° C. for 60 min and then at room temperature for a further 30 min. The hGS-(160–169) bound to the beaded polystyrene resin was deprotected and cleaved from the resin under conditions similar to those for film-bound hGS-(160–169); however, stirring was carried out only for 60 min at 0° C., which may account for the less efficient deprotection of the Arg(Tos) residues (as judged by the profile of the HPLC chromatogram in FIG. 2).

After removal of HF, the crude products were stirred with dry diethyl ether (15 ml each, 3×3 min), filtered off, dried in air for 20 min, and then extracted into 10% aqueous acetic acid (15 ml each, 3×15 min). Aliquots were analyzed by reverse-phase HPLC (before freezing and lyophilizing the remaining solution) to establish the purity of the peptides.

Figure 1B:
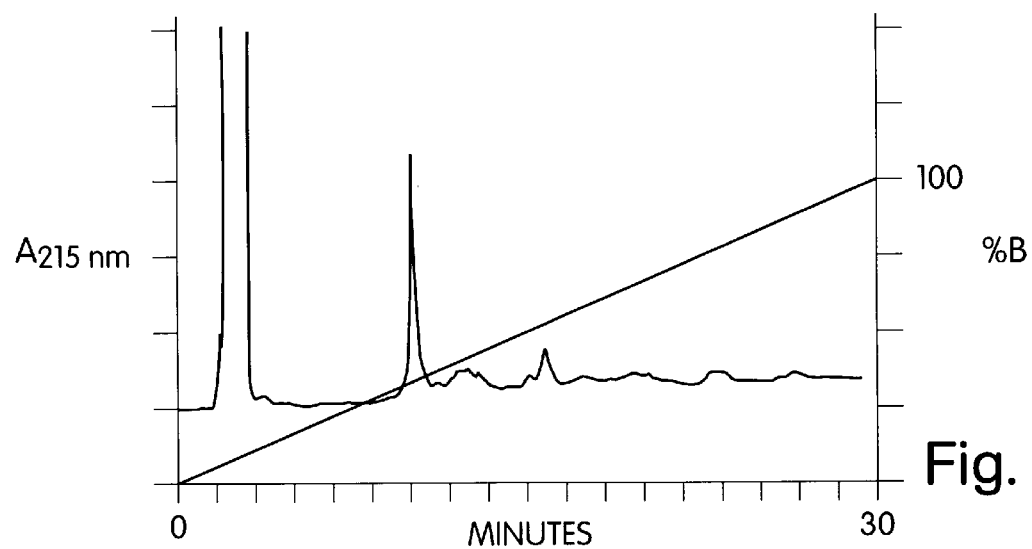
Figure 1C:
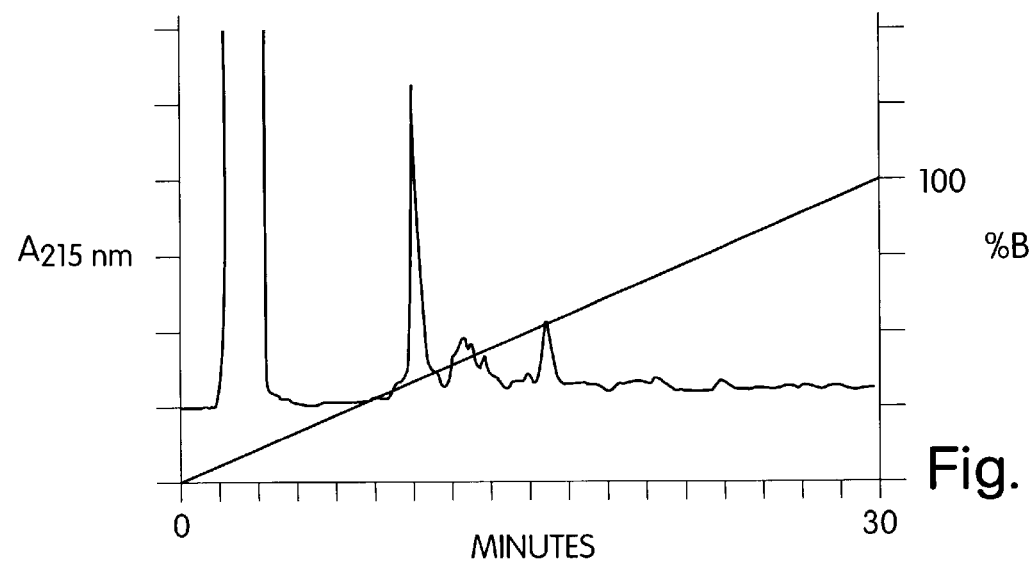
Figure 2:
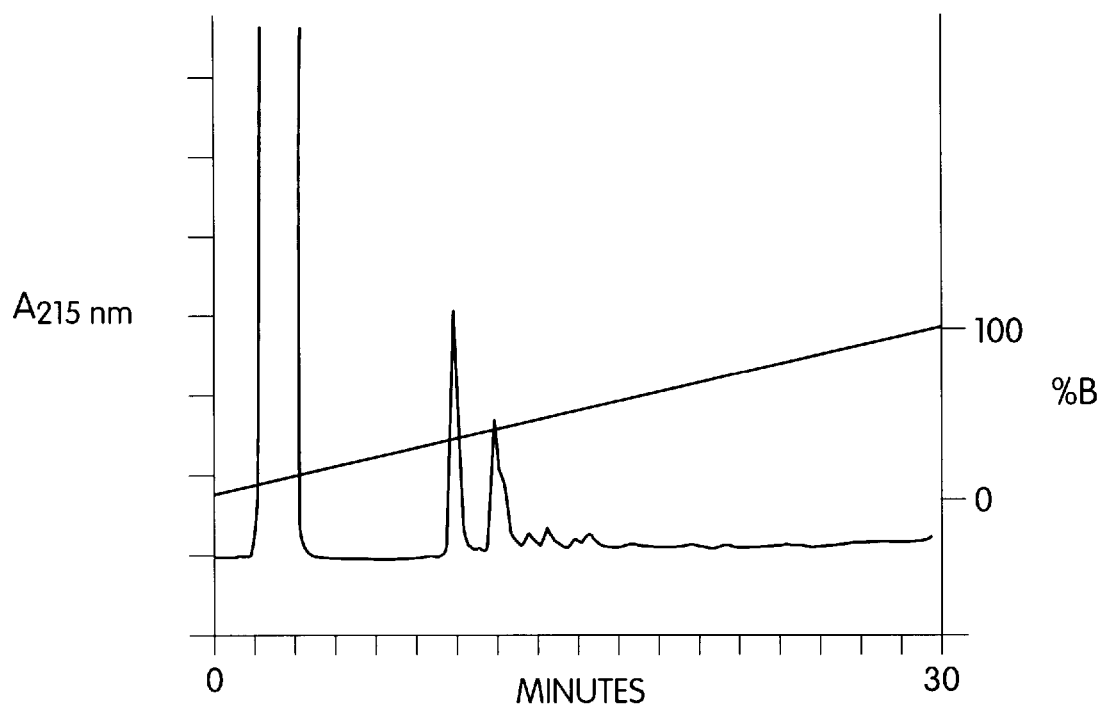
FIG. 2. Analytical HPLC chromatogram of crude human gelsolin fragment 160–169 synthesized on standard polystyrene beads. The HPLC conditions were the same as described in connection with FIG. 1.

FIGS. 1 and 2 show HPLC chromatograms of the unpurified peptides. It is apparent that the purity is good in each case, and in particular it can be seen that only minor peaks elute ahead of the target peak in the chromatogram, indicating the absence of significant amounts of deletion sequences. The crude hGS-(160–169) products were purified on a semi-preparative C$_{18}$ HPLC column, and the correct molecular weight (MW) of the purified hGS-(160–169) was confirmed by mass spectroscopic determination (MW found: 1285.8; MW calcd.: 1285.8).

Specific details on the synthesis of hGS-(160–169) on the four different supports are given in the following.

(a) Synthesis on the Boc-BHA derivatized PS-grafted XLPE film: The synthesis was initiated on 2.7 g of Boc-BHA derivatized PS-grafted XLPE film prepared according to Example 3(a) (initial substitution ca. 0.27 mmol of BHA/g) using a 70 ml reaction volume and a 100 ml SPPS reaction vessel. Boc-Lys(ClZ)$^{163}$, Boc-Arg(Tos)$^{168}$ and Boc-Gln$^{169}$ were each coupled three times to obtain satisfactory incorporation, as judged by quantitative Kaiser ninhydrin tests. Capping was carried out after coupling of residues number 160, 161, 162 and 163. The measured final loading was 0.13 mmol/g. An 82 mg sample of the peptide-carrying film was then subjected to the deprotection and release treatment, giving 7.1 mg of crude peptide.

(b) Synthesis on the Boc-BHA derivatized and PEO-modified PS-grafted XLPE film (Boc-BHA/PEO-film): The synthesis was initiated on 0.58 g of Boc-BHA/PEO-film prepared according to Example 4(d) (initial substitution ca. 0.11 mmol of BHA/g) using a 16 ml reaction volume and a 30 ml SPPS reaction vessel. Boc-Arg(Tos)$^{160}$ and Boc-Phe$^{166}$ were each coupled three times, and Boc-Arg(Tos)$^{168}$ four times, to obtain satisfactory incorporation, as judged by quantitative Kaiser ninhydrin tests. Capping was carried out after coupling of residues number 160, 161 and 164. The measured final loading was 0.062 mmol/g. A 140.5 mg sample of the peptide-carrying film was then subjected to the deprotection and release treatment, giving 9.3 mg of crude peptide.

c) Synthesis on the Boc-BHA derivatized and AM-modified PS-grafted XLPE film (Boc-BHA/AM-film): The synthesis was initiated on 0.71 g of Boc-BHA/AM-film prepared according to Example 4(c) (initial substitution ca. 0.12 mmol of BHA/g) using a 16 ml reaction volume and a 30 ml SPPS reaction vessel. Boc-Arg(Tos)$^{160}$, Boc-Val$^{164}$ and Boc-Phe$^{166}$ were each coupled three times, and Boc-Arg(Tos)$^{168}$ four times, to obtain satisfactory incorporation, as judged by quantitative Kaiser ninhydrin tests. Capping was carried out after coupling of residues number 160, 161 and 164. For unknown reasons, the measured substitution remained constant at about 0.12 mmol/g throughout the synthesis. It is, however, a well-known fact that ninhydrin analysis is not particularly well suited for polyamide-based types of supports. A 202.7 mg sample of the peptide-carrying film was subjected to the deprotection and release treatment, giving 10.5 mg of crude peptide.

(d) Synthesis on the Boc-BHA derivatized standard polystyrene beads: The synthesis was initiated on 1.5 g of p-methylbenzhydrylamine resin with a substitution of ca. 0.70 mmol/g. A 10 ml reaction volume and a 30 ml SPPS reaction vessel were employed. Boc-Arg(Tos)$^{168}$ was coupled four times, and Boc-Gln$^{169}$ was coupled three times, to obtain satisfactory incorporation, as judged by quantitative Kaiser ninhydrin tests. The measured final loading was ca. 0.21 mmol/g. A 176.8 mg sample of the peptide-bearing resin was subjected to the deprotection and release treatment, giving 15.9 mg of crude peptide.

EXAMPLE 7

Grafting of Polyethylene Tube with Polystyrene (a) Preparation of Cross-linked Polyethylene Tube A low density polyethylene tube with internal diameter 1.5 mm and outer diameter 2.5 mm was rolled up into a bundle of approx. 40 cm in diameter and irradiated with high-energy electrons (10 MeV) from an electron accelerator installed at the Risø National Laboratory. The absorbed dose was 307 kGy. Apart from an increased stiffness, the irradiated tube is visually and dimensionally indistinguishable from the unirradiated polyethylene tube.

(b) Preparation of Polystyrene-grafted Cross-linked Polyethylene Tubes

A 35% (v/v) styrene/methanol (technical grade) solution was bubbled thoroughly with argon for 13 min. to remove oxygen. The cross-linked tube, 154.23 g, was filled with the styrene/methanol solution and both ends were sealed. The tube was irradiated in a $^{60}$Co gamma-irradiation facility. The dose rate was approx. 1.2 kGy per hour, and the absorbed dose was 5.0 kGy. After the irradiation, the tube was allowed to stand for 24 hours to take advantage of the "post irradiation effect". The tube was opened and emptied by applying pressurized air. The tube was washed by allowing 2.0 liter of toluene (technical grade) to run slowly through the tube for 3 days followed by washing with 0.5 liter of methanol (technical grade). The tube was dried with pressurized air for two days. The tube weighed 172.16 g, indicating a polystyrene graft of 11.6%.

The tube appeared slightly white on the inside and more stiff than the irradiated polyethylene tube.

Functionalization/activation of Polystyrene-grafted Tubes (a) Preparation of Aminomethylated Tubes Each end of 12.3169 g of the polystyrene-grafted polyethylene tube (approx. 7.0 meter) was mounted onto an addition funnel under a dry nitrogen atmosphere. The tube was washed with a solution of 40.0 ml TFA/DCM (1:1 v/v) and emptied. A solution of 0.1950 g N-hydroxymethylphthalimide (1.10 mmol) in 40.0 ml TFA/

DCM (1:1 v/v) was allowed to run from one addition funnel to the other through the tube twice by lowering and raising the funnels. A solution of 5.00 ml trifluoromethanesulfonic acid (TFMSA) in 5.00 ml TFA was added in 1.00 ml portions to the TFA/DCM solution in the addition funnel.

The solution was passed forwards and backwards three times before the next portion was added to the other addition funnel. After addition of the last portion of TFMSA/TFA mixture, the solution was allowed to stand in the tube for 2.5 hours. The tube was emptied by applying pressurized air and washed by allowing 0.5 liter of dichloromethane, toluene and ethanol (technical grade) to run slowly (approx 0.5 liter/hour) through the tube. After washing, the tube was dried with pressurized air. The tube appeared white on the inside.

A solution of 450 ml ethanol (99%) and 50 ml hydrazine hydrate was passed slowly through the tube immersed in a water bath at 65° C. for 72 hours. The tube was washed by allowing 1.0 liter of hot ethanol followed by 0.20 liter DMF to run slowly (approx. 0.5 liter/hour) through the tube. Finally the tube was washed (neutralized) with 0.5 liter of DIEA/DCM (1:9 v/v) and 0.5 liter of DCM at room temperature.

The tube was cut into pieces of 1.0 meter length. Small samples were taken from different lengths of the tube and dried in vacuum. The degree of substitution (aminomethylation) was measured to $28.0\pm4.4\cdot10^{-6}$ mol $NH_2$ per gram tube by quantitative Kaiser ninhydrin test, indicating a substitution of approx. 0.27 mmol $NH_2$ per gram polystyrene in the tube. The aminomethylated tube appeared slightly white.

(b) Functionalizing of Aminomethylated Tube

The tube was attached to an electrically driven pump ("RHOCKC", Fluid- Mtering Inc.) allowing solutions to be pumped through the tube at variable flow speeds during washing procedures and in a closed circuit during reactions. The volume in each washing step was more than four times the internal volume in the tube, thus, for example, for a 3 meter tube more than 21 ml. In the washing steps, the solution was pumped through the tube at a rate of approx. 5 ml per min. Unless otherwise stated, the standard washing procedure after coupling was washing with DMF, toluene, DIEA/DCM (1:19 v/v) and DCM.

In the case of deprotection of Boc-protected derivatives, the tube was deprotected by treatment with a solution of TFA/DCM (1:1 v/v) for 30 min at a flow speed of 2 ml per min.

Unless otherwise stated, the standard washing procedure after deprotection was washing with DCM, DIEA/DCM (1:19 v/v), toluene, DIEA/DCM (1:19 v/v) and DCM.

(c) Preparation of Methylbenzydrylamine-derivatized Tube

Boc-protected 3-(4-methylbenzyhydrylamine)propionic acid was coupled as its HOBt ester to the $28.0\cdot10^{-6}$ mol $NH^2$ per gram aminomethylated tube, using the following procedure:

A solution of 0.10M DIC, HOBt and Boc-protected 3-(4-methylbenzyhydrylamine)propionic acid in DMF/DCM (1:1 v/v) was pumped through 3.0 meter aminomethylated tube in a closed circuit for two hours. The tube was washed according to the standard procedure. The coupling was repeated overnight Quantitative Kaiser ninhydrin tests on samples taken from each end of the tube indicated that approx. 40% of the initial amino groups had coupled to the Boc-protected MBHA reagent after the first coupling and 95% after the second coupling. The remaining free amino groups were acetylated using acetic anhydride/pyridine/ DCM (1:1:2 v/v), leaving only $0.050\cdot10^{-6}$ mol free amino groups per gram tube, as determined by quantitative Kaiser ninhydrin testing).

The tube was deprotected by treatment with TFA/DCM, using the standard deprotection and washing procedure. Subsequently, quantitative Kaiser ninhydrin test indicated MBHA derivatization of approx. $16.13-10^{-6}$ mol per gram tube.

(d) Preparation of Gly-PAM-derivatized Tube

Boc-protected Gly-PAM linker (Star Chemicals) was coupled as its HOBt ester to the $28.0\cdot10^{-6}$ mol $NH^2$ per gram aminomethylated tube, using the following procedure:

A solution of 0.30M DIC, HOBt and Boc-protected Gly-PAM linker in DMF/DCM (1:1 v/v) was pumped through approx 1,1 meter aminomethylated tube in a closed circuit overnight. The tube was washed according to the standard procedure. The coupling was repeated overnight using a concentration of 0.15M. Quantitative Kaiser ninhydrin tests on samples taken from each end of the tube indicated that approx. 97% of the initial amino groups had coupled to the Boc-protected PAM-Gly linker after the first coupling and more than 98% after the second coupling. The remaining free amino groups were acetylated using acetic anhydride/pyridine/DCM (1:1:2 v/v), leaving only $0.021\cdot10^{-6}$ mol free $NH_2$ per gram tube, as determined by quantitative Kaiser ninhydrin testing).

The tube was deprotected by treatment with TFA/DCM, using the standard deprotection and washing procedure. Subsequently quantitative Kaiser ninhydrin test indicated Gly-PAM derivatization of approx. $10.81\cdot10^{-6}$ mol per gram tube.

(e) Preparation of Fmomc-protected Gly-HMPHA-derivatized Tube

Hydroxymethylphenoxyacetic acid (HMPHA) was coupled as its HOBt ester to the $28.0\cdot10^{-6}$ mol $NH^2$ per gram aminomethylated tube, using the following procedure:

A solution of 0.1M HMPHA (Sigma), HOBt, DIC in DMF/DCM (1:1 v/v) was pumped through approx. 1.5 meter aminomethylated PEPS-tube in a closed circuit for two hours. The tube was washed by the standard procedure. The coupling was repeated four times. Quantitative Kaiser ninhydrin tests on samples taken from each end of the tube indicated that approx. 43% of the initial amino groups on the tube had coupled to the HMPHA linker after the first coupling and more than 94%, 97% and 98% after the second, third and fourth coupling. A solution of 0.5M Fmoc-GlyOH (Biochem) in a 2.6-dichlorobenzoylchloride (Aldrich)/ pyridine/DMF (2:2:25 v/v) was pumped through the tube for 72 hours and washed with DMF, toluene, DMF and DCM. A piece of the tube was deprotected by treatment with piperidine in DMF (1:1 v/v) for one hour. Subsequently quantitative Kaiser ninhydrin test indicated Fmoc-Gly-HMPHA derivatization of approx. $10.26\cdot10^{-6}$ mol per gram tube. The remaining free hydroxy groups were capped using benzoylchloride/Pyr/DMF (2:2:25 v/v) for one hour, followed by washing with DMF, toluene and DCM.

(f) Additional Measurement of the Degree of Substitution on Linker Functionalized Tubes The quantitative Kaiser ninhydrin test has previously resulted in too low values for Gly and MBHA derivatized polystyrene-grafted cross-linked polyethylene-materials. Therefore, the level of functionalization was further measured by attaching an amino acid to the linker derivatized tubes. For the three linker functionalized tubes: MBHA, PAM-Gly, and HMPHA-Gly, Fmoc-protected Leu was coupled and deprotected using the following procedure: The deprotected pieces of the tubes was connected in a series, washed with piperidine in DMF (1:4 v/v) for one hour, washed as standard and coupled with Fmoc-Leu using the following procedure: A solution of 0.25M HOBt, DIC and Fmoc-Leu-OPfp ester (Peninsula Laboratories) in DMF/DCM (1.1 v/v) was pumped through the tubes in a closed circuit for one hour. The tube was washed with DMF, toluene and DCM, benzyolated for 1 hour with a solution of benzoylchlorid/pyridine/DMF (4:4:50 v/v) followed by standard washing and deprotection of the Fmoc group by piperidine in DMF (1:4 v/v) for one hour, followed by washing with DMF, toluene, DIEA/DCM (1:4 v/v) and DCM. Quantitative Kaiser ninhydrin tests on samples taken from each end of the tubes indicated that the substitutions were 22.19 for the MBHA, 26.86 for the PAM-Gly and $15.93 \cdot 10^{-6}$ mol per gram tube for the Gly-HMPHA derivatized tubes.

EXAMPLE 8

PE-PDMAM Film

The purpose of these experiments was to develop an easy way to make hydrophilic films in two steps: One grafting step and one step to functionalize the film with primary amino groups.

(a) Preparation of Poly(N,N-dimethylacrylamide-co-acrylic Acid)—Grafted Cross-linked Polyethylene Films Low density polyethylene film with a thickness of 54 mm was irradiated with high-energy electrons (10 MeV) from an electron accelerator installed at the Risø National Laboratory. The absorbed dose was 300 kGy. The cross-linked polyethylene film was washed with toluene overnight and air-dried to constant weight overnight.

Two types of parallel experiment were conducted to find suitable conditions for grafting of poly-N,N-dimethylacrylamide (PDMAM) onto polyethylene. The first experiments were intended to find a suitable solvent system for grafting, the second series of experiments to optimize the grafting.

Pieces of film, approx. 1 g, were immersed into different solutions of N,N-dimethylacrylamide (DMAM, Fluka) and different solvent mixtures in 100 ml flasks. The solutions were bubbled thoroughly with argon for 15 min. to remove oxygen. The flasks were sealed with screwcaps and "parafilm" and placed in a closed aluminum container. The container was irradiated in a $^{60}Co$ gamma-irradiation facility at NUNC. The dose rate was approx. 1.2 kGy per hour. After irradiation, the film was taken out of the flasks and washed/rinsed extensively with toluene, hot ethanol, DCM and water, until the film had obtained constant weight after air drying. In the cases, where the films could not easily be separated from polymer in the solution, no attempts were made to dissolve or remove the homopolymer.

Several solvent systems were tried, including water, water/methanol, methanol/benzene, methanol/cyclohexane and benzene with from 14 to 33% v/v N,N-dimethylacrylamide and a gamma irradiation dose of 4.2 to 9.2 kGy. In solvent systems other than pure benzene, the grafting experiments resulted in large amounts of homopolymer in solution and/or a degree of grafting under 10%.

Dried benzene (p.a., dried over 4 A Mol. sieves (Fluka) for one week) was chosen as the solvent for grafting in the next experiments:

Parallel experiments with grafting in different mixtures of N,N-dimethylacrylamide/acrylic acid/benzene are summarized in table 1. The experiments were performed as described above.

TABLE 1

| No. | Monomer mixture | Benzene | | Graft % |
|---|---|---|---|---|
| 1 | A | 3 | 95 v/v | 16.65 |
| 2 | A | 10 | 90 v/v | 29.96 |
| 3 | A | 15 | 85 v/v | 34.51 |
| 4 | A | 20 | 80 v/v | -HP- |
| 3 | A | 25 | 75 v/v | -HP- |
| 6 | A | 30 | 70 v/v | -HP- |
| 7 | A | 35 | 65 v/v | -HP- |
| 8 | B | 5 | 95 v/v | 15.14 |
| 9 | B | 10 | 90 v/v | 37.94 |
| 10 | B | 15 | 85 v/v | 65.34 |
| 11 | B | 20 | 80 v/v | -HP- |
| 12 | B | 25 | 75 v/v | -HP- |
| 13 | B | 30 | 70 v/v | -HP- |
| 14 | B | 35 | 65 v/v | -HP- |

Monomer mixture A: N,N-dimethylacrylamide/acrylic acid: 10:1 v/v Monomer mixture B: N,N.dimethylacrylamide/acrylic acid: 30:1 v/v
"HP" = Homopolymer, the film could not easily be separated from polymer in the solution.
Gamma irradiation dose: between 5.8–7.9 kGy as measured on the front and backside of the aluminum container.

No. 10 in table 1 (65% graft) appeared stiff when dried. It was transparent and visually homogeneous. The 65% graft corresponds to about 40% PDMAA/PAA in the film. In water the film became soft and apparently "thick"—it swelled, and turned slightly white. In ethanol, methanol, DCM, DMF, DMSO, the film apparently swelled and remained visually transparent. This film was chosen for further functionalization to introduce a primary amino group.

(b) Functionaliziny of Poly(N,N-dimethylacrylamide-co-acrylic acid)-grafted Cross-linked Polyethylene Films Two types of modification have been performed on the 65% grafted film (no. 10 in table 1). One with 1.2-diaminoethane, creating a short linker between the film and the primary amino group to be further derivatized in e.g. solid phase peptide synthesis, and one type with a polyethylene glycol linker to the primary amino group. The polyethyleneoxide also functions as a "softener" in addition to increasing the hydrophilicity of the film.

Type 1

PE-Poly(DMAM-co-AA), approx. 65% graft, was derivatized with 1.2-diaminoethane using the following procedure:

PE-Poly(DMAM-co-AA), no. 10, approx. 65% graft was washed twice with 20 ml DCM and 20 ml toluene. The film was shaken with a solution of 1.2-diaminoethane (Aldrich)/DIC/DCM (2:1:20 v/v) overnight, followed by washing with DCM, DMF, ethanol (99%), DIEA/DCM (1:19 v/v) and DCM. The film was air-dried to constant weight. The film was indistinguishable from the starting PE-Poly(DMAM-co-AA)material. In water, the film became soft and appeared swelled. The level of substitution was measured to 0.092 mmol $NH^2$ per grain film by quantitative Kaiser ninhydrin test.

Type 2

PE-Poly(DMAM-co-AA), approx. 65% graft, was derivatized with amino end functionalized polyethyleneoxide using the following procedure:

0.17797 g PE-poly(DMAM-co-AA). no. 10, approx. 65% graft, was washed twice with 20 ml DCM and 20 ml toluene. The film was shaken with 1.00 g N-hydroxysuccinimide (Aldrich) in DIC/DCM (1:20 v/v) overnight and washed with DCM twice. The NHS ester modified film was shaken with a solution of 0,0-bis(2-aminopropyl)-polyethylene glycol 500 (average Mw 600 g/mol, Fluka) and DCM (2:1 v/v) for 48 hours, followed by washing with DCM, DMF, ethanol (99%), DIEA/DCM (1:19 v/v) and DCM. The film was dried in the air to constant weight, 0.20990 gram, indicating a modification of the film by approx. 18% polyethyleneoxide. The film appeared homogeneous and soft. In water the film remained soft and transparent The level of substitution was measured to 0.124 mmol $NH_2$ per gram film by quantitative Kaiser ninhydrin test.

EXAMPLE 9

Polystyrene-grafted Cross-linked Polyethylene-plates (a) Grafting of Polyethylene Plates with Polystyrene High and low density polyethylene plates with a thickness of 1.0 mm were cut into rectangular plates approx. 13 by 9 cm. Some of them were hot-pressed to give 96 (8 times 12) small concavities on one side of the plate.

(b) Preparation of Cross-linked Polyethylene Plates

Some of the polyethylene plates were irradiated with high-energy electrons (10 MeV) from an electron accelerator installed at the Risø National Laboratory. The absorbed dose was 314 kGy. The plates turned yellowbrown. Besides being coloured, the irradiated plates were visually and dimensionally indistinguishable from the unirradiated polyethylene plates.

(c) Preparation of Polystyrene-grafted Polyethylene Plates

Graft experiments were conducted, using cross-linked, non cross-linked, high and low density polyethylene plates. The following grafting procedure was used:

The polyethylene plates were immersed in a 30% (v/v) styrene/methanol (technical grade) solution in an aluminum container equipped with a lid. The solution was bubbled thoroughly with argon for 15 min. to remove oxygen and the container was closed. The container and its content were irradiated in a $^{60}$Co gamma-irradiation facility at NUNC. The dose rate was approx. 1.2 kGy per hour, and the absorbed dose was measured on the front and on the back of the container. After irradiation, the plates were removed and washed with toluene (technical grade), followed by methanol (technical grade), and again with toluene overnight The plates were air-dried to constant weight after three days. The plates appeared to have a matt surface. The non cross-linked plates, both the plane and the one with concavities, had inhomogeneities in the form of small blisters on the surface. It is the same phenomenon seen in the case of uncross-linked and grafted films. The cross-linked versions were still slightly miscoloured, but had a perfectly homogeneous surface. The plates with the small concavities appeared to have an inhomogeneous layer of graft on the edges of the concavities. Besides that, they were indistinguishable from the plane polyethylene plates. The gain in weight indicated a polystyrene graft between 5.02% and 12.3% with a gamma irradiation dose of 4.5 to 5.6 kGy.

The low density plates gave a higher graft yield than the high density ones. Table 2 summarizes the results from the graft experiments.

TABLE 2

| Type of PF | Geometry | X-linked | Irrad. dose: | % Graft |
| --- | --- | --- | --- | --- |
| HD | p | — | 4.5–5.6 kGy | 1.1 |
| LD | p | — | 3.9–5.2 kGy | 12.3 |
| LD | c | — | 3.9–5.2 kGy | 9.13 |
| LD | p | 314 kGy | 4.8–5.6 kGy | 7.43 |
| LD | c | 314 kGy | 4.8–5.6 kGy | 3.02 |
| LD | c | — | 4.8–5.6 kGy | 8.36 |

HD High density, LD = Low density.
Geometry: p = plane, c = hulls/concavities.
X-linked: Gives the absorbed dose. "—" = not cross-linked.

(d) Functionalization/action of Polystyrene-grafted Plates

Two series of experiments were carried out: The first series of experiments was modification of whole plates (approx. 13 by 9 cm). The other series were modifications of "pills", cut out of the plate. Each pill was 9.3 mm in diameter. The pills could be handled in ordinary laboratory equipment, in contrast to the chemical reactions on the big plates, which needed more unusual laboratory techniques.

(e) Preparation of Aminomethylated Polystyrene-grafted Cross-linked Polyethylene-plates The following procedure was typical for the aminomethylation of polystyrene-grafted cross-linked polyethylene-plates:

Nine polystyrene-grafted plates, approx. 115 g, with 5.0 to 8.4% polystyrene graft were washed with DCM. The plates were immersed into a solution of 0.34 g N-hydroxymethylphthalimide (Fluka) and 1.78 ml TFMSA per gram polystyrene on the plates, as calculated from the graft percents, in 1.00 liter TFA/DCM (1:1 v/v) in a glass jar with a lid. The plates were locked in a polypropylene array in order to keep them separated during the reaction. The jar and its content were slowly shaken overnight. The cross-linked plates turned slightly reddish.

The plates were rinsed with methanol, followed by DCM and again with methanol. After washing, the plates were air-dried. The plates appeared matt on the surface. The cross-linked versions were light brown.

The plates were immersed into a magnetically stirred solution of 450 ml ethanol (99%) and 50 ml hydrazine hydrate at 65° C. for 72 hours. The plates were repeatedly washed with hot ethanol. Finally, the plates were washed (neutralized) with DIEA/DCM (1:19 v/v) and DCM at room temperature and air-dried.

Samples of the plates were cut out into "pills" with a diameter of 9.3 mm and dried in vacuum. The degree of substitution (aminomethylation) was measured by quantitative Kaiser ninhydrin test to 3.34, 3.75, and $3.23 \times 10^{-6}$ mol $NH^2$ per gram plate for plates with 8.4, 7.4 and 5.0% polystyrene graft, corresponding to a substitution between 0.043 and 0.068 mmol $NH_2$ per gram polystyrene on the surface of the plate.

(f) Functionalizing of Aminomethylated Polystyrene-grafted Cross-linked Polyethylene-plates The following procedure was typical for coupling of Boc-protected amino acids to the aminomethylated polystyrene-grafted cross-linked polyethylene-plates.

The plates were washed/rinsed with DIEA/DCM (1:19 v/v) and by DCM in an open jar before being shaken in a solution of 0.1M Boc-protected amino acid in DIC/DCM/DMF (3:100:100) for two hours. The plates were covered with the reaction solution at all times. The plates were washed extensively with DCM, followed by ethanol, DIEA/

DCM (1:19 v/v) and DCM. The coupling and washing procedure were repeated.

The plates were acetylated (capped) by immersing them into a solution of acetic anhydride/pyridine/DCM (1:1:2 v/v) for two hours, followed by washing in DCM, DIEA/DCM (1:19 v/v) and DCM. The plates were deprotected by shaking in a solution of TFA/DCM (1:1 v/v) for 30 min. The plates were washed extensively with DCM, followed by ethanol, DIEA/DCM (1:19 v/v) and DCM. Samples were cut out for quantitative Kaiser ninhydrin test after each coupling, capping and deprotection step.

(g) Preparation of Gly-derivatized Polystyrene-grafted Cross-linked Polyethylene-plates Plates with a Gly linker attached to the surface were prepared as described above. E.g. for a cross-linked, plane, 5.0% grafted aminomethylated plate ($3.23 \cdot 10^{-6}$ mol per gram), quantitative Kaiser ninhydrin test indicated that approx. 65% and 93% of the initial amino groups had coupled after the first and the second coupling.

The remaining free amino groups were acetylated. After deprotection quantitative Kaiser ninhydrin test indicated a Gly derivatization of approx $2.275 \cdot 10^{-6}$ mol per gram plate. Considering the previously described low values measured by the quantitative Kaiser ninhydrin test, for Gly derivatized polystyrene-grafted cross-linked polyethylene-materials, the substitution is probably about 30 to 40% higher.

(h) Functionalization of Polystyrene-grafted Cross-linked Polyethylene-plates, Cut into Pills In this example an uncross-linked 1.00 mm HD-PEPS-plate with 11,1% polystyrene graft was used. The plate was cut into "pills", each 9,3 mm in diameter. The pills were handled in the same laboratory equipment as the polystyrene-grafted cross-linked polyethylene-films allowing for the pills to be shaken with various solvents and reagent mixtures in a convenient way.

Unless otherwise stated, the polystyrene-grafted cross-linked polyethylene-material was washed and deprotected following this standard protocol:

After each coupling: Washing by shaking with methanol twice for one nun, DCM for 10 min., DIEA/DCM (1:19 v/v) for one min. twice and DCM for one min. four times.

Capping: Shaking the pills with a solution of acetic anhydride/pyridine/DCM (1:1:2 v/v) for two hours, followed by washing with methanol twice for one min., DCM for 10 min., DIEA/DCM (1:19 v/v) for one min. twice and DCM for one min. four times.

Deprotection: Shaking with a solution of TFA/DCM (1:1 v/v) for 30 min., followed by washing with methanol twice (1 min.), DCM (10 min.), DIEA/DCM (1:19 v/v) for one min. twice and DCM for one 1 min. four times.

Two types of derivatization of the polystyrene-grafted cross-linked polyethylene-material were performed. A normal aminomethylation and derivatization, giving derivatives of the hydrophobic material, and a high level of aminomethylation followed by introduction of a Boc-protected Gly linker and blocking of the excess amino groups with a hydrophilic ethylene glycol acid, giving a more hydrophilic version of the material analogous to the hydrophilic polystyrene-grafted cross-linked polyethylene-film.

(i) Preparation of Gly-derivatized Polystyrene-grafted Cross-linked Polyethylene-plates Cut Into Pills 40 pills, 2,8018 g, corresponding to 0,3110 g polystyrene, were washed with DCM. The pills were shaken with N-hydroxymethyl phthalimide (16,53 mg, 93,3 mmol) in a solution of 30 ml TFA/DCM (1:1 v/v) for 10 min.

Six 1.00 ml portions of TFMSA in TFA (1:5 v/v) were added 30 min. apart. The pills were shaken slowly overnight. The white pills were washed twice with DCM and then washed with methanol twice for one min., DCM for 10 min., DIEA/DCM (1:19 v/v) for one min. twice and DCM for one min. four times. The pills were shaken with a solution of hydrazine hydrate in ethanol (1:4 v/v) at 60°–70° C. for three days (72h.), followed by washing with 95% ethanol for one min. 8 times, DCM for 10 min., DIEA/DCM (1:19 v/v) for one min. twice and DCM for one min. four times.

Boc-protected Gly was coupled twice to the aminomethylated pills, using the following procedure:

A solution of 0.10M DIC and Boc-protected GlyOH (Peninsula Laboratories) in DCM was added to the pills and shaken overnight.

The pills were acetylated and deprotected according to the protocol. The degree of substitution after the different steps as measured by quantitative Kaiser ninhydrin test is summarized in table 3. The substitution is given as amino groups both per square cm and per gram plate.

TABLE 3

|  | mmol/cm$^2$ | μmol/g |
| --- | --- | --- |
| PEPS—CH2NH2: | 435.1 | 8.305 |
| —GlyBoc: | 5.3 | 0.104 |
| —GlyBoc, Capped: | 4.4 | 0.087 |
| —GlyNH2: | 335.6 | 6.563 |

(j) Preparation of Boc-protected Amino Acid-derivatized Polystyrene-grafted Cross-linked Polyethylene-pills In order to evaluate the accessibility for coupling of the first amino acid, Boc-protected GlyOH, AlaOH, 3-(4-methylbenzyhydrylamino)propionic acid and ArgOH (Peninsula Laboratories) were coupled parallel to the Gly derivatized polystyrene-grafted cross-linked polyethylene-plates. Boc-GlyOH and Boc-AlaOH were coupled overnight in DIC/DCM (1.5:100 v/v). Boc-Arg and Boc-MBHA linker were coupled overnight as preformed HOBt esters in DMF (0.1M). The couplings were repeated twice. The level of remaining free amino groups as measured by quantitative Kaiser ninhydrin test after the first and second coupling is summarized in table 4. The substitution is given as amino groups both per square cm and per gram plate.

TABLE 4

|  | 1st coupling | | 2nd coupling | |
| --- | --- | --- | --- | --- |
|  | mmol/cm$^2$ | μmol/g | mmol/cm$^2$ | μmol/g |
| —GlyGlyBoc: | 7.1 | 0.133 | 0.4 | 0.008 |
| —GlyAlaBoc: | 9.8 | 0.183 | 11.3 | 0.211 |
| —GlyMBHABoc: | 5.5 | 0.103 | 5.3 | 0.099 |
| —GlyArgBOC: | 33.2 | 0.622 | 22.7 | 0.415 |

Table 3 indicates that the efficiency of coupling is more than 99.9% for BocGly and more than 93.2% for BocArgOH to the Gly-derivatized polystyrene-grafted cross-linked polyethylene-plates.

(k) Preparation of Gly-derivatized Hydrophilic Polystyrene-grafted Cross-linked Polyethylene-plates Cut into Pills 40 pills, 2.937 g, corresponding to 0.3101 grain polystyrene were washed with DCM. The pills were shaken with N-hydroxymethyl phthalimide (0.3826 g, 3.289 mmol) in 30 ml TFA/DCM (1:1 v/v) for 10 min. Six 1.00 ml portions of TFMSA in TEA (1:5 v/v) were added 30 min. apart The pills were shaken slowly overnight The pills were washed twice with DCM and then washed with methanol twice for one min., DCM for 10 min, DIEA/DCM (1:19 v/v) for one min. twice and DCM for one min. four times. After drying, the yellow pills have gained 207.3 mg. The pills were shaken with a solution of hydrazine hydrate in ethanol (1:4 v/v) at 60°–70° C. for three days (72 h.). The yellow pills turned white after one hour. The pills were washed with 93% ethanol for one min. 8 times, DCM for 10 min., DIEA/DCM (1:19 v/v) for one min. twice and DCM for one min. four times.

Boc-protected Gly was coupled to the aminomethylated plates and the remaining amino groups blocked with 3,6,9-trioxadecanoic acid, using the following procedure:

16 pills (approx 1.1 g) were shaken with a 15 ml solution of 0.1M Boc-protected GlyOH and DIC for 30 min. The pills were washed twice with DCM and coupled with a 1.0M solution of 3,6,9-trioxadecanoic acid and DIC in DCM for one hour. They were then washed twice with DIEA/DCM (1:19 v/v) for one min. and four times with DCM for 1 min. The pills were coupled a second time overnight with 3,6,9-trioxadecanoic acid and washed according to the protocol.

The pills were acetylated and deprotected according to the protocol. The degree of substitution after the different steps as measured by quantitative Kaiser ninhydrin test is summarized in table 5. The substitution is given as amino groups both per square cm and per gram plate.

TABLE 5

|  | mmol/cm$^2$ | µmol/g |
|---|---|---|
| PEPSCH2NH2: | 2919.7 | 55.024 |
| —PEO, GlyBoc: | 3.9 | 0.072 |
| —PEO, GlyBoc, Capped: | 6.7 | 0.119 |
| —PEO, GlyNH2: | 430.8 | 7.743 |

(l) Preparation of Boc-protected Amino Acid-derivatized Hydrophilic Polystrene-grafted Cross-linked Polyethylene-pills In order to evaluate the accessibility for coupling of the first amino acid, Boc-protected GlyOH, AlaOH, 3-(4-methybenzyhydrylamino)propionic acid and ArgOH were coupled parallel to the Gly derivatized hydrophilic polystyrene-grafted cross-linked polyethylene-plates. Boc-GlyOH and Boc-AlaOH were coupled overnight in DIC/DCM (1.5:100 v/v). Boc-Arg, Boc-MBHA linker were coupled overnight as preformed HOBt esters in DMF (0.1M). The couplings were repeated twice.

The level of remaining free amino groups as measured by quantitative Kaiser ninhydrin test after the first and second coupling is summarized in table 4. The substitution is given as mmol amino groups both per square cm and per gram plate.

TABLE 6

|  | 1st coupling | | 2nd coupling | |
|---|---|---|---|---|
|  | mmol/cm$^2$ | µmol/g | mmol/cm$^2$ | µmol/g |
| —GlyGlyBoc: | 28.5 | 0.502 | 4.4 | 0.079 |
| —GlyAlaBoc: | 27.6 | 0.485 | 11.9 | 0.209 |
| —GlyMBHABoc: | 20.3 | 0.359 | 6.6 | 0.114 |
| —GlyArgBOC: | 21.3 | 0.368 | 19.5 | 0.333 |

Table 6 indicates that the efficiency of coupling is more than 99.0% for BocGly and more than 95.5% for BocArgOH to the Gly-derivatized hydrophilic polystyrene-grafted cross-linked polyethylene-plates.

General Comments

PAS-IR Measurements on Polystyrene-grafted Cross-linked Polyethylene-materials

Photoacoustic spectroscopy in the infrared range (PAS-IR) was used to evaluate the reactions on the surfaces qualitatively. The plates and tubes were compared before and after the grafting with polyethylene and polystyrene samples, confirming that polystyrene dominates the surface of the grafted materials. The phthalimido group was monitored at approx. 1720 cm$^{-1}$. Total disappearance of the peak after hydrazinolysis, indicated the complete demasking of phthalimide functionality.

General Reflections on Washing Procedures for Polystyrene-grafted Cross-linked polyethylene-materials The washing procedures in some cases included toluene. Toluene swells polystyrene and partly polyethylene, allowing reagents and other solvents to be removed in depth. The intention by washing the materials with methanol or ethanol after e.g. washing with DCM, was to "squeeze out" reagents or solvents from the surface. Polystyrene is not swelled by methanol or ethanol. DMF and DCM were used to swell the polystyrene part of the material and dissolve and remove reagents and solvents.

EXAMPLE 10

Peptide Synthesis, Polystyrene-grafted Cross-linked Polyethylene-tube

The decapeptideamide, H-Tyr-Asp-Ala-Lys-Ser-Gly-Phe-Lys-Thr-Ala NH$_2$ was synthesized on the tube using conventional BOC protection strategy.

No attempts to optimize the couplings were made.

Synthetic Protocol

The tube was connected to an electrically driven pump ("RHOCKC", Fluid-Metering Inc.) allowing solutions to be pumped through the tube at variable flow speeds during washing procedures and in a closed circuit during deprotection with TFA/DCM, capping and coupling with the different Boc-protected amino acids. Kaiser ninhydrin tests of samples cut out from the tube were used to evaluate the progress of the synthesis.

The fully protected peptide was assembled by step wise coupling, employing the following protocol:

1) Deprotection of Boc-protected Derivatives

The tube was treated with a solution of TFA/DCM (1:1 v/v) for 30 min. at a flow speed of 2 ml per min.

2) Neutralization

Washing with DCM, DIEA/DCM (1:19 v/v), toluene, DIEA/DCM (1:19 v/v) and DCM for 5 min. each at a flow speed of approx. 5 ml per min.

3) Kaiser Ninhydrin Test

4) Coupling of Boc-protected Amino Acids

The tube was reacted with a solution of DIC (0.2M), HOBt (0.2M) and Boc-protected amino acid (0.2M) in DMF/DCM (1:1 v/v) for one hour unless otherwise stated.

5) Washing After Coupling

Washing with DMF, toluene, DIEA/DCM (1:19 v/v) and DCM for 5 min. each at a flow speed of approx 5 ml per min.

6) Kaiser Ninhydrin Test

A coupling was occasionally repeated (step 4 to 6) until the coupling had gone to near completeness. The degree of completeness was determined by the level of unreacted free amino groups, as measured by quantitative or qualitative Kaiser ninhydrin tests.

Where appropriate, acetylation (capping) was performed.

7) Capping

The tube was treated with a solution of acetic anhydride/pyridine DCM (1:1:2 v/v) for 30 min. at a flow speed of 2 ml per min.

8) Washing After Capping

Washing with DCM, DIEA/DCM (1:19 v/v), toluene, DIEA/DCM (1:19 v/v) and DCM for 5 min. each at a flow speed of approx 5 ml per min.

9) Kaiser Ninhydrin Test.

The next Boc-protected amino acid was coupled by repetition of the cycle, steps 1 to 8.

(a) Synthesis of H-Tyr-Asp-Ala-Lys-Ser-Gly-Phe-Lys-Thr-Ala NH$_2$ on Polystyrene-grafted Cross-linked Polyethylene-tube The tube used, was a MBHA derivatized tube of approx 1.09 meter in length, prepared as previously described. The volume in each washing step was more than four times the internal volume of the tube.

The substitution was measured to 0.017 mmol NH$_2$ per gram.

The fully protected Boc-Ala-Thr(Bzl)-Lys(ClZ)-Phe-Gly-Ser(Bzl)-Lys(ClZ)-Ala-Asp(OBzl)-Tyr(BrZ)-MBHA-tube was assembled by step wise coupling, employing the standard protocol previously described.

The following deviations from the protocol was made:

Tyr$^1$ was coupled three times with 0.1M DIC, BocTyr (BrZ) in DCM.

Asp$^2$ was coupled once with 0.15M DIC, BocAsp(OBzl) in DCM and once with 0.15M of its preformed HOBt ester in DMF/DCM (3:7 v/v).

Ala$^3$ was coupled twice as its preformed HOBt ester in DMF/DCM (3:7 v/v).

Lys$^4$ was coupled twice as its preformed HOBt ester (0.15M) in DMF/DCM (3:7 v/v) and once with 0.2M DIC, BocLys(ClZ) in DCM and once as a standard coupling.

Thr$^9$ was coupled twice as standard, once with 0.2M DIC, BocThr(Bzl) in DCM and the fourth time as standard.

Ala$^{10}$ was coupled the second time in 0.2M DIC, BocAla in DCM.

Capping was performed after Asp$^2$, Ala$^3$, Lys$^4$ and Gly$^6$.

The fully protected decapeptide was deprotected with TFA/DCM and washed according to the protocol prior to HF cleavage. The final loading was $8.29 \pm 0.38 \cdot 10^{-6}$ mol per gram measured at four different points along the tube.

(b) HF Cleavage of Peptide

The tube was cut open along its length and additionally cut into small pieces of approx. 0.2 cm. The pieces of tube were washed with DCM, ethanol (99%) and DCM twice before drying in vacuum in an exsiccator for one hour. 1.64036 gram (approx. 54 cm) of the peptide carrying pieces of tube was stirred with anisole in HF (10 ml, 1:1 v/v) for one hour at 0° C. and then at room temperature for additional 20 min. After removal of the HF, the crude products were stirred with dry diethyl ether (10 ml, technical) three times for 10 min., filtered off, air-dried for 10 min. and then extracted into a solution of acetic acid in water (1:9 v/v) three times for 10 min. The acetic acid-water solutions were combined and freezed dried overnight. The raw peptide, 8.63 mg, was analyzed by reverse-phase HPLC.

We claim:

1. A cross-linked polyethylene substrate grafted with at least one polystyrene chain wherein the polystyrene chain contains at least one chemical functionality that facilitates the formation of an anchoring linkage between the polystyrene chain and another chemical species, and wherein the polyethylene substrate is cross-linked before grafting by irradiating said polyethylene substrate with a radiation dose of at least 50 kGy resulting in incipient gel formation.

2. A polystyrene-grafted cross-linked polyethylene substrate according to claim 1, wherein the chemical functionality is a functionality facilitating the formation of an anchoring linkage between the polystyrene chain and an at least N-protected and optionally carboxyl terminal derivatized amino acid.

3. A polystyrene-grafted cross-linked polyethylene substrate according to claim 2, wherein the functionality is derived from an amino group-containing moiety selected from the group consisting of: amino-substituted alkyl, amino- and aryl-substituted alkyl, and amino- and alkylaryl-substituted alkyl; and the functionality comprises a spacer group derived from a member selected from the group consisting of 4-(haloalkyl)aryl-lower alkanoic acid, a Boc-aminoacyl-4-(oxymethyl)aryl-lower alkanoic acid, an N-Boc-p-acylbenzhydrylamine, an N-Boc-4'-lower alkyl-p-acylbenzhydrylamine, an N-Boc-4'-lower alkoxy-p-acylbenzhydrylamine, and a 4-hydroxymethylphenoxy-lower alkanoic acid.

4. A polystyrene-grafted cross-linked polyethylene substrate according to claim 2, wherein the functionality is a functionality such that the anchoring linkage is a linkage ensuring substantially permanent anchoring linkage of the species attached to the substrate.

5. A polystyrene-grafted cross-linked polyethylene substrate according to claim 4, wherein the functionality does not contain a spacer group, or contains a spacer group that will ensure substantially permanent anchoring linkage of the species attached to the substrate.

6. A polystyrene-grafted cross-linked polyethylene substrate according to claim 4, wherein the linkage is a linkage derived from an amino-substituted alkyl group.

7. A polystyrene-grafted cross-linked polyethylene substrate according to claim 6, wherein the functionality comprises a spacer group derived from a member selected from the group consisting of: a straight chain omega-aminoalkanoic acid and branched chain omega-aminoalkanoic acid.

8. A polystyrene-grafted cross-linked polyethylene substrate according to claim 2, wherein the chemical functionality facilitating the formation of an anchoring linkage between an at least N-protected and optionally carboxy terminal derivatized amino acid and the polystyrene chain is, or is derived from a group selected from the group consisting of:

a chloro-, bromo- or iodo-substituted alkyl, an amino-substituted alkyl, an amino- and aryl-substituted alkyl, an amino- and alkylaryl-substituted alkyl, and an hydroxy-substituted alkyl.

9. A polystyrene-grafted cross-linked polyethylene substrate according to claim 8, wherein said chemical functionality is, or is derived from a member selected from the group consisting of:

chloromethyl, aminomethyl,

α-aminobenzyl

α-amino-2, α-amino-3 or α-amino-4-methylbenzyl, and hydroxymethyl.

10. A polystyrene-grafted cross-linked polyethylene substrate according to claim 8, wherein the functionality comprises a spacer group such that a peptide or protein chain attached through the anchoring linkage will be cleavable from the polystyrene moiety substantially without degradation of said chain.

11. A polystyrene-grafted cross-linked polyethylene substrate according to claim 1, wherein the grafted polystyrene chain bears at least one further substituent which is such that the polymer-grafted cross-linked polyethylene substrate is swellable by water or aqueous media.

12. A polystyrene-grafted cross-linked polyethylene substrate according to claim 11, wherein the substituent is selected from the group consisting of: polyoxyethylene and oligooxyethylene moieties, polyacrylamides and oligoacrylamides, polyamides and oligoamides, saccharides, including dextrans, cellulose, agarose, starch, and agar, peptides, amino acids, polycations, polyanions, polyisothiocyanates, and hydrophilic natural substances.

13. A polystyrene-grafted cross-linked polyethylene substrate according to claim 1, wherein the estimated peak molecular weight of the polystyrene chains grafted to the cross-linked polyethylene not including optional substituents, is at least 200,000.

14. A polystyrene-grafted cross-linked polyethylene substrate according to claim 1, which has been prepared from a cross-linked polyethylene substrate in the form of a sheet or a film of thickness in the range of 25 to 100 μm, and in which the degree of polystyrene chain grafting is in the range of 5–800% by weight.

15. A polystyrene-grafted cross-linked polyethylene substrate according to claim 1, which is a member selected from the group consisting of a sheet, film, bead, pellet, disc, ring, tube, rod, net, tray, microliter plate, and multi-bladed stick.

16. A polystyrene-grafted cross-linked polyethylene substrate according to claim 1, in which another chemical species has been coupled to the at least one polystyrene chain.

17. A polystyrene-grafted cross-linked polyethylene substrate according to claim 1, wherein the other chemical species is selected from the group consisting of a DNA, DNA analogue, amino acid, peptide and protein.

18. In a method for facilitating the spectrophotometric monitoring of an antigen/antibody reaction, in an analytical procedure, wherein the improvement comprises using a peptide-bearing polystyrene-grafted cross-linked polyethylene substrate according to claim 1 as a light-transparent or light reflecting carrier material.

19. A method according to claim 18, wherein said antigen is a peptide synthesized on and remaining anchored to the polystyrene-grafted polyethylene substrate.

20. A method according to claim 19, wherein said antigen is a peptide coupled to the polystyrene-grafted polyethylene substrate.

21. A method according to claim 18, wherein said monitoring entails the use of an ELISA technique.

22. A polystyrene-grafted cross-linked polyethylene substrate according to claim 1, wherein the polystyrene chain further bears substituents which are not reactive under the conditions prevailing in peptide synthesis.

* * * * *

UNITED STATES PATENT AND TRADEMARK OFFICE
CERTIFICATE OF CORRECTION

PATENT NO. : 5,886,104
DATED : March 23, 1999
INVENTOR(S) : Walther B. Pedersen, ET AL.

It is certified that error appears in the above-identified patent and that said Letters Patent is hereby corrected as shown below:

In the claims:

amend claim 15 to read as follows:

15. A polystyrene-grafted cross-linked polyethylene substrate according to claim 1, which is a member selected from the group consisting of a sheet, film bead, pellet, disc, ring, tube, rod, net, tray, [microliter] microtiter plate, and multi-bladed stick.

amend claim 17 to read as follows:

17. A polystyrene-grafted cross-linked polyethylene substrate according to claim [1] 16, wherein the other chemical species is selected from the group consisting of a DNA, DNA analogue, amino acid, peptide and protein.

Signed and Sealed this

Seventh Day of December, 1999

Attest:

Q. TODD DICKINSON

*Attesting Officer*  *Acting Commissioner of Patents and Trademarks*